US011342054B2

(12) United States Patent
Rozier et al.

(10) Patent No.: US 11,342,054 B2
(45) Date of Patent: May 24, 2022

(54) SYSTEM USING NFC-ENABLED MEDICINE PACKAGING TO ESTABLISH A NO-LOGIN, AUTHENTICATED AND CONTEXTUALIZED TWO-WAYS DATA FLOW BETWEEN A PATIENT AND A PHARMACEUTICAL MANUFACTURER

(71) Applicant: Xerox Corporation, Norwalk, CT (US)

(72) Inventors: David Rozier, Bernin (FR); Nicolas Guerin, Notre Dame de Mésage (FR)

(73) Assignee: Xerox Corporation, Norwalk, CT (US)

( * ) Notice: Subject to any disclaimer, the term of this patent is extended or adjusted under 35 U.S.C. 154(b) by 754 days.

(21) Appl. No.: 15/342,383

(22) Filed: Nov. 3, 2016

(65) Prior Publication Data

US 2018/0121615 A1    May 3, 2018

(51) Int. Cl.
| | |
|---|---|
| *G16H 10/65* | (2018.01) |
| *G16H 50/20* | (2018.01) |
| *H04W 4/80* | (2018.01) |
| *H04L 29/06* | (2006.01) |
| *H04W 12/06* | (2021.01) |

(Continued)

(52) U.S. Cl.
CPC ............. *G16H 10/65* (2018.01); *G16H 50/20* (2018.01); *H04L 63/0428* (2013.01); *H04L 63/0492* (2013.01); *H04L 63/08* (2013.01); *H04W 4/80* (2018.02); *H04W 12/02* (2013.01); *H04W 12/033* (2021.01); *H04W 12/06* (2013.01)

(58) Field of Classification Search
CPC ......... G16H 10/65; G16H 50/20; H04W 4/80; H04W 12/06; H04W 12/02; H04L 63/0492; H04L 63/0428; H04L 63/08

USPC .......................................................... 705/2
See application file for complete search history.

(56) References Cited

U.S. PATENT DOCUMENTS

| | | | |
|---|---|---|---|
| 8,838,983 B2 * | 9/2014 | Sharma ................... | G06F 21/64 713/176 |
| 2009/0045963 A1 * | 2/2009 | Vigneron ......... | G06K 19/07798 340/572.8 |

(Continued)

FOREIGN PATENT DOCUMENTS

WO    WO2013121356 A2    8/2013

OTHER PUBLICATIONS

Zoutman et al., "A Call for the Regulation of Prescription Data Mining", Oct. 31, 2000, 3 pages.

(Continued)

*Primary Examiner* — Robert A Sorey
*Assistant Examiner* — Kimberly A. Sass
(74) *Attorney, Agent, or Firm* — Fay Sharpe LLP

(57) ABSTRACT

A system and method to establish a no-login authenticated and contextualized two-ways data flow between a medicine user and the pharmaceutical manufacturer. Near Field Communication (NFC) technology, enabling short-range communication between two compatible devices is utilized via a writeable NFC tag carried by a medication package. The writeable NFC tag includes medication information, anti-counterfeiting information, as well as data about the patient and the prescription. The NFC tag may be read by a user device associated with the patient, enabling the user device to merge this data with the patient's feedback, send this rich flow in a secure way to the manufacturer, who in turn is now able to provide rich contextual guidance to the patient.

20 Claims, 11 Drawing Sheets

(51) Int. Cl.
*H04W 12/02* (2009.01)
*H04W 12/033* (2021.01)

(56) References Cited

U.S. PATENT DOCUMENTS

| | | | |
|---|---|---|---|
| 2014/0188502 A1 | 7/2014 | Defrank et al. | |
| 2014/0229387 A1* | 8/2014 | Chow | G06Q 20/3829 |
| | | | 705/71 |
| 2015/0106113 A1* | 4/2015 | Reddy | G06Q 30/0185 |
| | | | 705/2 |
| 2017/0293738 A1* | 10/2017 | Bender | G16H 10/60 |
| 2018/0130548 A1* | 5/2018 | Fisher | G06Q 20/3227 |

OTHER PUBLICATIONS https://en.wikipedia.org/wiki/Electronic_prescribing, "Electronic Prescribing", Wikipedia.
http://www.informationmediary.com/med-ic, "MED-IC Smart Labels".
http://www.vttresearch.com/media/news/nfc-aid-for-the-visually-impaired, "NFC Aid for the Visually Impaired", Jan. 18, 2012.
http://www.rxmedic.com/blog/74-smart-labels-smart-receipts-what-s-next.html, "Smart Labels. Smart Receipts. What's Next?", Jun. 18, 2013, Dr. Charles Shively.
http://www.rxscan.com/products/smart-label-design.html, "Smartlabel Design & Print".
http://www.pharmaceutical-technology.com/features/featurethe-smart-approach-to-pharma-packaging/featurethe-smart-approach-to-pharma-packaging-1.html; "The Smart Approach To Pharma Packaging".
www.physicianspractice.com/e-prescribing/safe-e-prescribing-primer-practices, "Safe E-Prescribing: A Primer for Practices", Torrieri, M. (2012).

* cited by examiner

SYSTEM USING NFC-ENABLED MEDICINE PACKAGING TO ESTABLISH A NO-LOGIN, AUTHENTICATED AND CONTEXTUALIZED TWO-WAYS DATA FLOW BETWEEN A PATIENT AND A PHARMACEUTICAL MANUFACTURER

BACKGROUND

The subject disclosure relates to the medical arts, the secure communications arts, the packaging arts and the like.

The pharmaceutical industry general attempts to communicate with patients and users of their products. There are a variety of reasons why pharmaceutical companies desire communication with these users. For example, obtaining feedback directly from the patients regarding adverse effects of treatments provides more concise information than anecdotal information reported by medical professionals. Feedback regarding the efficacy and efficiency of treatments is more direct from a patient, rather than the information moderated by the patients' doctors.

Other reasons for effective communication between patients/users and the pharmaceutical companies include enhancing the adherence of patients to their prescription, fighting against counterfeit medicine, identifying candidates for clinical trials, educating patients to insure they understand their treatment and how to maximize the efficiency of the treatment, identifying potentially dangerous prescriptions (and drug interactions), understanding how medication is prescribed, and the like. Some pharmaceutical companies, in addition, collect prescription data for further analysis (it is possible to build individual physician-prescribing profiles, so that manufacturers can focus some commercial actions to specific practitioners, e.g., prescription data-mining.

This desire for communication is not only exhibited by the pharmaceutical companies, but is also manifested by the patients. In particular, patients are signaling that they need a stronger accompaniment (i.e., understandable treatment information) during their treatment. FIG. 1, illustrates the reasons behind patient dissatisfaction regarding their respective treatments, e.g., high treatment costs, dealing with side effects, wait times, difficult medication regime, confusing medication literature, lack of support, etc. As shown in FIG. 1, several of the noted areas of dissatisfaction correlate with the pharmaceutical companies' desire to establish patient-company communications.

Currently, pharmaceutical companies lack sufficient means of communicating information to patients regarding treatments and other products. This is especially important when considering the need to update patients on potential drug interactions, as well as assisting in alleviating some of the dissatisfaction identified by patients during treatment. Unfortunately, establishing communication between pharmaceutical companies and patients is difficult, particularly as secure communications must be established to ensure compliance with various privacy concerns, e.g., HIPAA.

Attempts to relay certain information to patients have been attempted, for example so-called "smart labels", such as those identified by (see http://www.rxscan.com/products/smart-label-design.html, "SMARTLABEL DESIGN & PRINT"). Some solutions include patient data, like current medications being taken (see http://www.rxmedic.com/blog/74-smart-labels-smart-receipts-what-s-next.html, "SMART LABELS. SMART RECEIPTS. WHAT'S NEXT?", Jun. 18, 2013, Dr. Charles SHIVELY). Unfortunately, these solutions rely on printed information (barcode, QR codes), and do not allow interactions with the pharmaceutical company.

With respect to providing adherence guidance and collecting some limited feedback, technologies such as Stora Enso Pharma DDSi solution (see http://www.pharmaceutical-technology.com/features/featurethe-smart-approach-to-pharma-packaging/featurethe-smart-approach-to-pharma-packaging-1.html; "THE SMART APPROACH TO PHARMA PACKAGING") or Med-IC (see http://www.informationmediary.com/med-ic, "MED-IC SMART LABELS"), have been used. However, these technologies are problematic in that the solution is not richly contextualized with patient's data, and is also relying on more costly and rigid devices (USB for transfer to PC) rather than being light, cheap and flexible as it is possible through NFC tags.

Attempts to utilize NFC-tags have met with limited success, primarily because in most cases, such NFC-tags are not writable tags. As a consequence, the information dispensed to the user is static, rather than personalized. For example, see the NFC-enabled packaging, developed by VTT Technical Research Centre of Finland in January 2012 (see http://www.vttresearch.com/media/news/nfc-aid-for-the-visually-impaired, "NFC AID FOR THE VISUALLY IMPAIRED", Jan. 18, 2012), for the visually impaired. When a code comes in contact with an NFC-enabled device, a user can download the product and dosage information, which can be played back using a phone or computer. No customization or feedback to the pharmaceutical company is possible with such an implementation.

Other attempts to alleviate the problems discussed above include U.S. Patent Publication No. 2014/0188502, published Jul. 3, 2014, by Defrank et al., and entitled "PRESCRIPTION SMART LABEL SYSTEM" mentions a smart package for medicine providing NFC interactions. The patent describes a prescription smart label system for tracking patient use of prescription medications to assist in medication treatment to monitor their progress toward recovery. The system aims at assisting the patient to take is medication, and at automatically sending usage data, e.g. pills taken, to the pharmacy or doctor. However, this labeling system does not provide a communication channel with the pharmaceutical company, and does not allow user feedback. See also, counterfeit detection using NFC, as described in PCT Patent No. WO2013121356A2, published Aug. 22, 2013, by Maheshwar Reddy, S. R. and entitled "NEAR FIELD COMMUNICATION (NFC) BASED COUNTERFEIT PRODUCT IDENTIFICATION SYSTEM"). However, this reference relies on server communication to detect a counterfeit product.

Accordingly, what is needed is a solution that utilizes personalized prescription and medication information on an easily accessible and programmable platform that incorporates advancements in NFC-enabled, inexpensive tags, providing patient guidance, pharmacy anti-counterfeit detection, secure communication of patient and prescription information, and allows for direct contact between the pharmaceutical company manufacturing the medication and the patient taking the medication.

INCORPORATION BY REFERENCE

U.S. Patent Publication No. 2014/0188502, published Jul. 3, 2014, by Defrank et al., and entitled "PRESCRIPTION SMART LABEL SYSTEM";

PCT Patent No. WO2013121356A2, published Aug. 22, 2013, by Maheshwar Reddy, S. R. and entitled "NEAR FIELD COMMUNICATION (NFC) BASED COUNTERFEIT PRODUCT IDENTIFICATION SYSTEM";

ZOUTMAN et al., "A CALL FOR THE REGULATION OF PRESCRIPTION DATA MINING", Oct. 31, 2000, 3 pages;
https://en.wikipedia.org/wiki/Electronic_prescribing, "ELECTRONIC PRESCRIBING", Wikipedia;
http://www.informationmediary.com/med-ic, "MED-IC SMART LABELS";
http://www.vttresearch.com/media/news/nfc-aid-for-the-visually-impaired, "NFC AID FOR THE VISUALLY IMPAIRED", Jan. 18, 2012;
http://www.rxmedic.com/blog/74-smart-labels-smart-receipts-what-s-next.html, "SMART LABELS. SMART RECEIPTS. WHAT'S NEXT?", Jun. 18, 2013, Dr. Charles SHIVELY;
http://www.rxscan.com/products/smart-label-design.html, "SMARTLABEL DESIGN & PRINT";
http://www.pharmaceutical-technology.com/features/featurethe-smart-approach-to-pharma-packaging/featurethe-smart-approach-to-pharma-packaging-1.html; "THE SMART APPROACH TO PHARMA PACKAGING";
http://www.physicianspractice.com/e-prescribing/safe-e-prescribing-primer-practices, "SAFE E-PRESCRIBING: A PRIMER FOR PRACTICES", Torrieri, M. (2012), are incorporated herein by reference in their entirety.

BRIEF DESCRIPTION

In one embodiment of this disclosure, described is a near-field communication (NFC)-enabled medication packaging system. The system includes a server that comprises a processor in communication with memory, a near-field communications transceiver in data communication with the processor and memory, and a data storage in communication with the processor, the data storage storing a public key and a private key. The memory of the server stores instructions which are executed by the processor to initialize a tag of a medicine package with medication data corresponding to a medication contained therein, and sign the tag using the private key to establish authentication of the medication contained in the medicine package. The instructions also direct the processor to receive encrypted data from a user device via a secure communications link over a computer network, the encrypted data including at least one of prescription data and patient data, decrypt the received data to retrieve the at least one of the prescription data and the patient data, and generate personalized guidance specific to the patient in accordance with at least one of the prescription data and the patient data. In addition, the instructions direct the processor to communicate, via the secure communications link over the computer network, the personalized guidance specific to the patient to the user device.

In another embodiment of this disclosure, described is a near-field communication (NFC)-enabled medication packaging method. The method includes initializing, with a processor of a server, a tag of a medicine package with medication data corresponding to a medication contained in the package, and signing the tag, by the server, using a private key to establish authentication of the medication contained in the medicine package. The method further includes receiving data encrypted with a public key associated with the private key from a user device via a secure communications link over a computer network, the encrypted data including at least one of prescription data and patient data. The method also includes decrypting the received data via the private key to retrieve the at least one of the prescription data and the patient data, and generating personalized guidance specific to the patient in accordance with at least one of the prescription data and the patient data. Additionally, the method includes communicating, via the secure communications link over the computer network, the personalized guidance specific to the patient to the user device, wherein at least one of the initializing, signing, decrypting, generating, and communicating is performed by the processor of the server.

In still another embodiment of this disclosure, described is a computer-implemented method for computer-implemented method for near-field communication (NFC)-enabled medication packaging. The method includes writing at least one of a medication name, a medication packaging, a batch number, and an expiration date on a tag of a medicine package with medication data corresponding to a medication contained therein. The method further includes signing the tag using a private key to establish authentication of the medication contained in the medicine package, and receiving data encrypted with a public key associated with the private key from a user device via a secure communications link over a computer network, the encrypted data including at least one of prescription data and patient data. The method also includes decrypting the received data via the private key to retrieve the at least one of the prescription data and the patient data, receiving, from the user device via the secure communications link over the computer network, user feedback data representative of a use of the medication by the patient, and analyzing the received feedback data. In addition, the method includes generating personalized guidance specific to the patient in accordance with the analyzed user feedback data and at least one of the prescription data and the patient data, and communicating, via the secure communications link over the computer network, the personalized guidance specific to the patient to the user device

DETAILED DESCRIPTION

Disclosed herein are systems and methods for setting up a secure, convenient, and rich data channel between patients taking a medical treatment and the manufacturer of the treatment. In varying embodiments discussed hereinafter, the systems and methods utilize near-field communication ("NFC") technology, in that an NFC tag is incorporated into or affixed to medicine packaging, the tag is appropriately programmed at the time of dispensing, and facilitates establishing a secure channel from the consumer's NFC-enabled user device, e.g., smartphone, to the pharmaceutical manufacturer's information system.

In accordance with one embodiment, the systems and methods set forth hereinafter enable a synthetic system whereby the aforementioned use of NFC-enabled components are integrated within an illustrative healthcare system's organization. As previously discussed, pharmaceutical industries are suffering from the lack of an efficient communication channel with patients treated with their products. The necessity for better communications are numerous, and include, for example and without limitation, feedback about adverse effects of treatments, feedback about efficacy and efficiency of treatments, adherence of patients to their prescription, counterfeit medicine, identify candidates for clinical trials, educate patients, to assure they understand their treatment and how to maximize its efficiency for example, identify potentially dangerous prescriptions, understand how the medication is prescribed, and collect prescription data for further analysis (it is possible to build individual physician-prescribing profiles, so that manufacturers can focus some commercial actions to specific practitioners. Prescription data-mining for this purpose is already a commercial activity. (See ZOUTMAN et al., "A CALL FOR THE REGULATION OF PRESCRIPTION DATA MINING", Oct. 31, 2000, 3 pages, the entire disclosure of which is incorporated by reference herein.)

Figure 1:
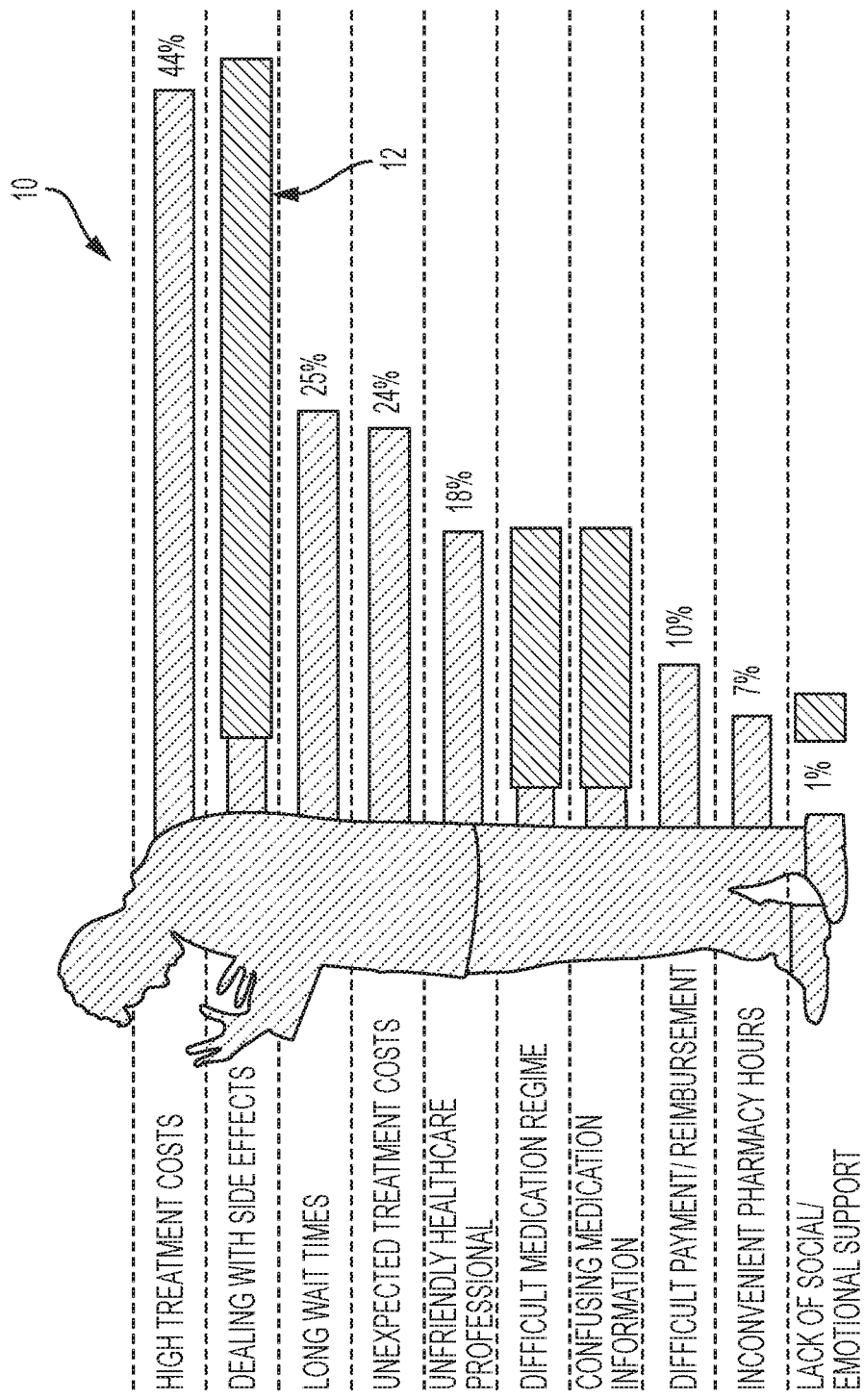
FIG. 1 is an illustration of patient motivation as to dissatisfaction relating to treatments.

Reversely, patients are signaling that they need a stronger accompaniment during their treatment. FIG. 1, as discussed above, shows the motives of dissatisfaction of patients regarding their treatments. Accordingly, the systems and methods set forth hereinafter include, for example and without limitation, a method of using writable-NFC-enabled medicine packaging in order to establish a no-login (therefore easier) channel, an authenticated and secure data flow, a contextualized data flow, in the sense that it is a merge of manufacturing data, prescription data, patient records data, and patient declarative information, a personalized channel from a medicine user to the pharmaceutical manufacturer, therefore useful for the industry, a personalized channel from the pharmaceutical manufacturer to the medicine user, therefore useful for the patient, a simple counterfeit medication detection solution for the patient. It will be appreciated that the systems and methods described herein provide an implementation of such a method in a way that is compatible with usual prescription and medicine delivery policies.

According to one embodiment, described herein is a method to establish a no-login authenticated and contextualized two-ways data flow between a medicine user and the pharmaceutical manufacturer. This is achieved using Near Field Communication (NFC) technology, that enables short-range communication between two compatible devices, which can be smartphones, dedicated devices (NFC reader/writer), or NFC tags. A medicine package carries a writable NFC tag, containing data about the patient, the medicine, and the prescription, that allows the patient's smartphone to merge these data with patient's feedback, send this rich flow in a secure way to the manufacturer, who in turn is now able to provide rich contextual guidance to the patient.

Figure 2:
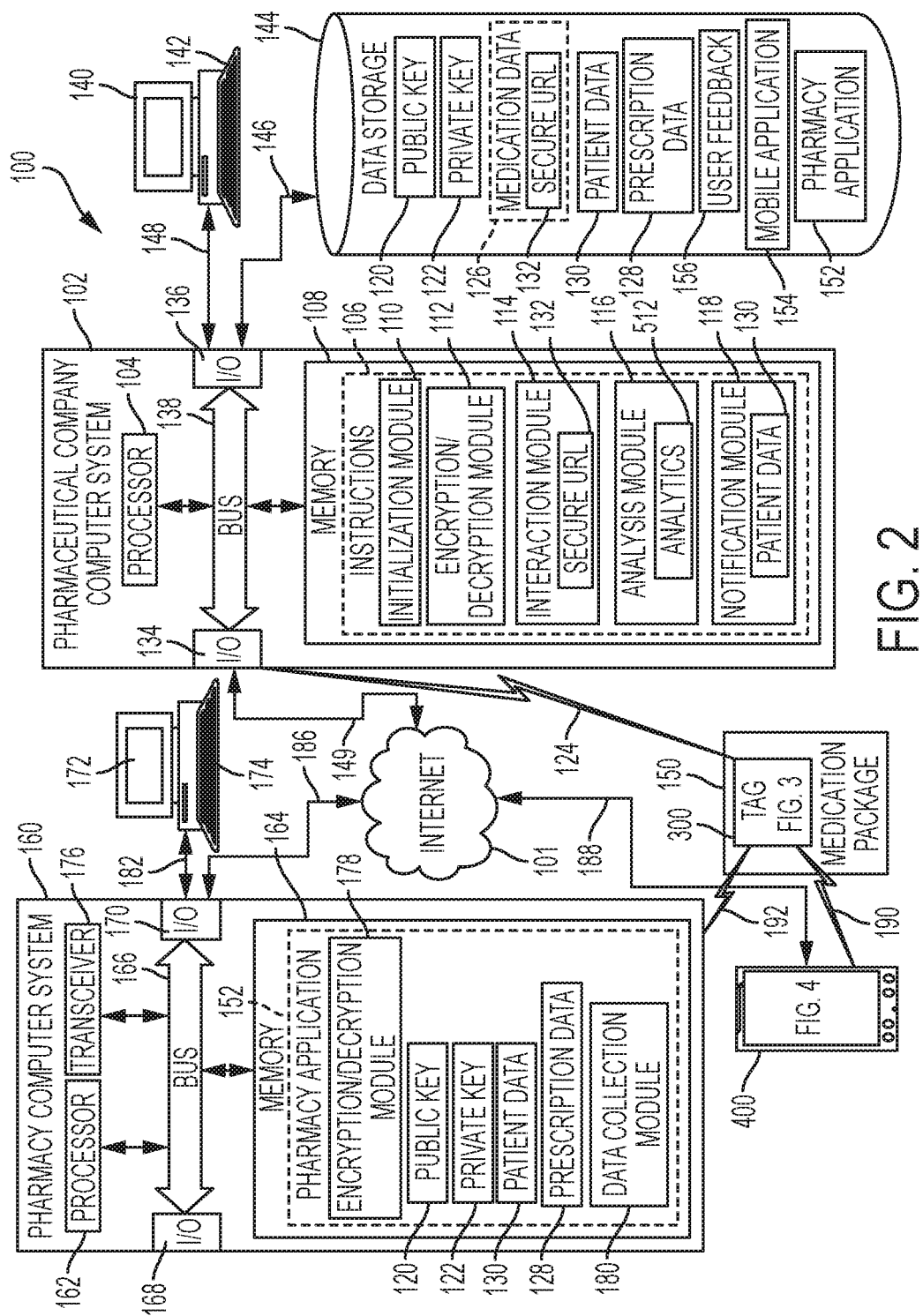
FIG. 2 is an illustration of a NFC-enabled medication packaging bi-directional communication system in accordance with one embodiment of the subject application.

Referring now to FIG. 2, there is shown a Near-Field Communication ("NFC")-enabled medication packaging system 100 configured for bi-directional data communication between a patient's user device and a pharmaceutical manufacturer computer system in accordance with one aspect of the subject disclosure. It will be appreciated that the various components depicted in FIG. 2 are for purposes of illustrating aspects of the exemplary embodiment, and that other similar components, implemented via hardware, software, or a combination thereof, are capable of being substituted therein.

As shown in FIG. 2, the NFC-enabled medication packaging bi-directional communication system 100 includes pharmaceutical company computer system 102 (hereinafter computer system 102) configured to interact with a plurality of different devices and components, as are illustrated therein. The exemplary computer system 102 includes a processor 104, which performs the exemplary method by execution of processing instructions 106 that are stored in memory 108 connected to the processor 104, as well as controlling the overall operation of the computer system 102.

The instructions 106 include an initialization module 110 that is configured to initialize an NFC-enabled tag 300 in accordance with one embodiment of the subject application. As will be understood, the initialization module 110 facilitates the establishment of an NFC communications link 124 between the pharmaceutical company computer system 102 and the tag 300 embedded or affixed to medication packaging 150, as discussed in greater detail below. The initialization module 110 may include hardware/software, e.g., an NFC transceiver, capable of establishing short-range communications links with the tag 300. In accordance with one embodiment, the initialization module 110 is tasked with communicating medication information 126, along with a secure URL 132, to the memory 304 of the tag 300. As discussed in greater detail below, the medication data 126 may include, for example and without limitation, the name (trade name, chemical name, etc.) of the medication, the expiration date, the manufacturing date, the batch number, etc. In such an embodiment, the medication data 126 may be signed with a private encryption key 122, which may be utilized by pharmacies for authentication purposes, i.e., authenticate medication as opposed to generic, etc.

The instructions 106 may also include an encryption/decryption module 112 that utilizes public key encryption (PKI) in the form of a public key 120 and a private key 122 pair for secure communications and authentication purposes. According to one embodiment, the encryption/decryption module 112 may be used to encrypt/sign medication data 126 during manufacturing of the medication, decrypt patient data 130, prescription data 128, or the like, received from a patient as described in detail below. It will be appreciated that the encryption/decryption module 112 may function in concert with the interaction module 110 during digital signing operations, as well as with other modules implemented by the processor 104 of the pharmaceutical company computer system 102, as set forth herein.

The instructions 106 may also include an interaction module 114 hosting a secure web page, e.g., identified by a secure uniform resource locator ("URL") 132 via which various entities may interact with the computer system 102, e.g., the pharmacy computer system 160, the user device 400, and the like, as discussed in greater detail below. According to one example embodiment, data sent and received over the Internet 101 to and from the pharmaceutical company computer system 102 may use encrypted protocols, e.g., HTTPS, preventing reading by a "man-in-the-middle", i.e., intercepted by a third party. In accordance with one embodiment, the interaction module 114 may provide prompts and communications to the patient via the secure URL 132, direct messaging, emails, etc., soliciting feedback 156, providing warnings, side effects, drug interactions, present personalized guidance, etc., to the patient via the user device 400. In some embodiments, the interaction module 114 may dynamically generate web forms to collect user feedback 156.

The instructions 106 depicted in FIG. 2 may further include an analysis module 116, which may analyze the aforementioned user feedback 156, generate contextualized information regarding patient usage of the medication, generate results reflecting population data analytics, and the like. According to one embodiment, the output of the analysis module 116 may be utilized by the interactions module 114 in the generation of web forms, personalized guidance, engagement with the patient, and the like. Also illustrated in the instructions 106 of the computer system 102 in FIG. 2 is a notification module 118 that may communicate the aforementioned dynamic web forms, provide alerts to the user device 400 and pharmacy computer systems 160, and the like.

The various components of the pharmaceutical company computer system 102 may all be connected by a data/control bus 138. The processor 104 of the computer system 102 is in communication with an associated data storage 144 via a link 146. A suitable communications link 146 may include, for example, the public switched telephone network, a proprietary communications network, infrared, optical, or other suitable wired or wireless data communications. The data storage 144 is capable of implementation on components of the computer system 102, e.g., stored in local memory 108, i.e., on hard drives, virtual drives, or the like, or on remote memory accessible to the computer system 102.

The associated data storage 144 corresponds to any organized collections of data (e.g., encryption information, research information, medical information, side effects, treatment plans, manufacturing dates, manufacturing lots, packaging information, tag information, medical practitioner information, pharmacological information, user information, prescription information, etc.) used for one or more purposes. Implementation of the associated data storage 144 is capable of occurring on any mass storage device(s), for example, magnetic storage drives, a hard disk drive, optical storage devices, flash memory devices, or a suitable combination thereof. The associated data storage 144 may be implemented as a component of the computer system 102, e.g., resident in memory 108, or the like.

In one embodiment, the associated data storage 144 may include data corresponding to a public key 120, private key 122, medication data 126, URL information 132, patient data 130, prescription data 128, user feedback 156, mobile device applications 154, pharmacy computer system applications 152, and the like. It will be appreciated that the mobile device application 154 may be an iOS, ANDROID, MICROSOFT, BLACKBERRY, or other suitably compatible application capable of running on a mobile device, e.g., a cellular smartphone. In some embodiments, the mobile device 400 may utilize a thin client interface (e.g., a web browser such as CHROME, SAFARI, DOLPHIN, FIREFOX, EDGE, or other mobile web browsers) to facilitate interactions between the mobile device 400 and the pharmaceutical computer system 102, as discussed in greater detail below. The pharmacy computer system application 152 may be implemented as a computer program compatible with operating systems provided by GOOGLE, APPLE, MICROSOFT, or proprietary operating systems utilized by the pharmacy computer system 160, as discussed in greater detail below. In other embodiments, the pharmacy computer system 160 may a thin client, i.e., web browser, capable of interacting with the pharmaceutical company computer system 102, as discussed in greater detail below.

The computer system 102 may include one or more input/output (I/O) interface devices 134 and 136 for communicating with external devices. The I/O interface 134 may communicate, via communications link 148, with one or more of a display device 140, for displaying information, such estimated destinations, and a user input device 142, such as a keyboard or touch or writable screen, for inputting text, and/or a cursor control device, such as mouse, trackball, or the like, for communicating user input information and command selections to the processor 104.

It will be appreciated that the NFC-enabled medication packaging bi-directional communication system 100 is capable of implementation using a distributed computing environment, such as a computer network, which is representative of any distributed communications system capable of enabling the exchange of data between two or more electronic devices. It will be further appreciated that such a computer network includes, for example and without limitation, a virtual local area network, a wide area network, a personal area network, a local area network, the Internet, an intranet, or the any suitable combination thereof. Accordingly, such a computer network comprises physical layers and transport layers, as illustrated by various conventional data transport mechanisms, such as, for example and without limitation, Token-Ring, Ethernet, or other wireless or wire-based data communication mechanisms. Furthermore, while depicted in FIG. 2 as a networked set of components, the system and method are capable of implementation on a stand-alone device adapted to perform the methods described herein.

The computer system 102 may include a computer server, workstation, personal computer, cellular telephone, tablet computer, pager, combination thereof, or other computing device capable of executing instructions for performing the exemplary method.

According to one example embodiment, the computer system 102 includes hardware, software, and/or any suitable combination thereof, configured to interact with an associated user, a networked device, networked storage, remote devices, or the like.

The memory 108 may represent any type of non-transitory computer readable medium such as random access memory (RAM), read only memory (ROM), magnetic disk or tape, optical disk, flash memory, or holographic memory. In one embodiment, the memory 108 comprises a combination of random access memory and read only memory. In some embodiments, the processor 104 and memory 108 may be combined in a single chip. The network interface(s) 134, 136 allow the computer to communicate with other devices via a computer network, and may comprise a modulator/demodulator (MODEM). Memory 108 may store data the processed in the method as well as the instructions for performing the exemplary method.

The digital processor 104 can be variously embodied, such as by a single core processor, a dual core processor (or more generally by a multiple core processor), a digital processor and cooperating math coprocessor, a digital controller, or the like. The digital processor 104, in addition to controlling the operation of the computer 102, executes instructions 106 stored in memory 108 for performing the method outlined in FIG. 6.

The various components of the pharmaceutical company computer system 102 may all be connected by a data/control bus 138. The processor 104 of the computer system 102 is in communication with an associated data storage 144 via a link 146. A suitable communications link 146 may include, for example, the public switched telephone network, a proprietary communications network, infrared, optical, or other suitable wired or wireless data communications. The data storage 144 is capable of implementation on components of the computer system 102, e.g., stored in local memory 108, i.e., on hard drives, virtual drives, or the like, or on remote memory accessible to the computer system 102.

The associated data storage 144 corresponds to any organized collections of data (e.g., encryption information, research information, medical information, side effects, treatment plans, manufacturing dates, manufacturing lots, packaging information, tag information, medical practitioner information, pharmacological information, user information, prescription information, etc.) used for one or more purposes. Implementation of the associated data storage 144 is capable of occurring on any mass storage device(s), for example, magnetic storage drives, a hard disk drive, optical storage devices, flash memory devices, or a suitable combination thereof. The associated data storage 144 may be implemented as a component of the computer system 102, e.g., resident in memory 108, or the like.

In one embodiment, the associated data storage 144 may include data corresponding to a public key 120, private key 122, medication data 126, URL information 132, patient data 130, prescription data 128, user feedback 156, mobile device applications 154, pharmacy computer system applications 152, and the like.

The computer system 102 may include one or more input/output (I/O) interface devices 134 and 136 for communicating with external devices. The I/O interface 134 may communicate, via communications link 148, with one or more of a display device 140, for displaying information, such estimated destinations, and a user input device 142, such as a keyboard or touch or writable screen, for inputting text, and/or a cursor control device, such as mouse, trackball, or the like, for communicating user input information and command selections to the processor 104.

It will be appreciated that the NFC-enabled medication packaging bi-directional communication system 100 is capable of implementation using a distributed computing environment, such as a computer network, which is representative of any distributed communications system capable of enabling the exchange of data between two or more electronic devices. It will be further appreciated that such a computer network includes, for example and without limitation, a virtual local area network, a wide area network, a personal area network, a local area network, the Internet, an intranet, or the any suitable combination thereof. Accordingly, such a computer network comprises physical layers and transport layers, as illustrated by various conventional data transport mechanisms, such as, for example and without limitation, Token-Ring, Ethernet, or other wireless or wire-based data communication mechanisms. Furthermore, while depicted in FIG. 2 as a networked set of components, the system and method are capable of implementation on a stand-alone device adapted to perform the methods described herein.

The computer system 102 may include a computer server, workstation, personal computer, cellular telephone, tablet computer, pager, combination thereof, or other computing device capable of executing instructions for performing the exemplary method.

According to one example embodiment, the computer system 102 includes hardware, software, and/or any suitable combination thereof, configured to interact with an associated user, a networked device, networked storage, remote devices, or the like.

The memory 108 may represent any type of non-transitory computer readable medium such as random access memory (RAM), read only memory (ROM), magnetic disk or tape, optical disk, flash memory, or holographic memory. In one embodiment, the memory 108 comprises a combination of random access memory and read only memory. In some embodiments, the processor 104 and memory 108 may be combined in a single chip. The network interface(s) 134, 136 allow the computer to communicate with other devices via a computer network, and may comprise a modulator/demodulator (MODEM). Memory 108 may store data the processed in the method as well as the instructions for performing the exemplary method.

The digital processor 104 can be variously embodied, such as by a single core processor, a dual core processor (or more generally by a multiple core processor), a digital processor and cooperating math coprocessor, a digital controller, or the like. The digital processor 104, in addition to controlling the operation of the computer 102, executes instructions 106 stored in memory 108 for performing the method outlined in FIGS. 6-8.

The system 100 depicted in FIG. 2 may include at least one tag 300, affixed to a medication package 150. It will be appreciated that the tag 150 may be inserted inside the package 150 prior to sealing the package 150 with medication therein. In other embodiments, the tag 150 is embedded within the package 150 during the manufacture of the package 150 itself, i.e., embedded within layers (of paper medication packaging), embedded within caps/lids (plastic packaging), embedded within labels which may be printed at a pharmacy and affixed to suitable medication packages 150, or myriad other methods of fastening the tag 300 to a medication package 150 regardless of the form which the medication package 150 takes. It will further be appreciated that the medication itself (not shown) may be manufactured separately from the packaging 150 and the tag 300, and assembly of the medication package 150 by the pharmaceutical company (i.e., the entity associated with the computer system 102) includes insertion/attachment of the tag 300. A functional block representation of the tag 300 is depicted in FIG. 3, discussed in detail hereinafter.

Figure 3:
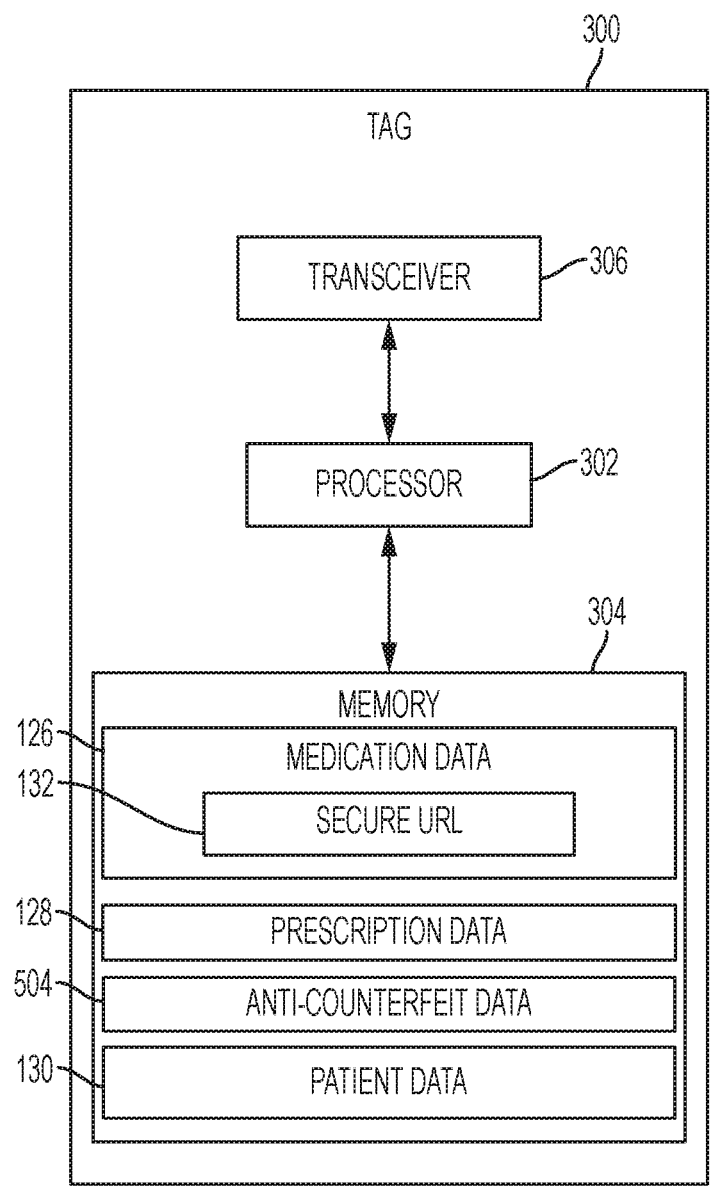
FIG. 3 is a functional block diagram of a tag for use in the NFC-enabled medication packaging bi-directional communication system in accordance with one embodiment of the subject application.

With regard to FIG. 3, the tag 300 may be implemented as an unpowered tag (power externally supplied by another device) such as those offered by Gemalto, EM Microelectronic, Infineon or NXP (e.g., PN512). In particular embodiments, the tag 300 may adhere to the ISO/IEC 18092, 14443, and 21481 standards, or to the NFC Forum standards, as will be appreciated by those skilled in the art. As will be understood, the tag 300 is representative of a low-cost Near Field Communication (NFC) device that is capable of communication with an NFC-enabled user device over a short distance, e.g., up to 10 cm, which may be affixed, in various manners, to articles of manufacture and utilized for myriad purposes, including those which are set forth in the subject application.

As shown in FIG. 3, the tag 300 includes a processor 302 in communication with memory 304 and a transceiver 306. The processor 302 may include a random number generator and other suitable components to facilitate the systems and methods discussed hereinafter. The memory 304 may comprise non-volatile and/or volatile memory capable of storing various types of data. The tag 300 may utilize symmetric cryptography (3DES, AES, PKI, etc.) or asymmetric cryptography (RSA, ECC, etc.). In accordance with one embodiment, the memory 304 includes read/write capabilities, and may store information received from the pharmaceutical company computer system 102, e.g., medication data 126, secure URL 132, as well as information received from the pharmacy computer system 160, e.g., prescription data 128, patient data 130, and the like. Regarding the first data, i.e., the medication data 126 and the secure URL 132, this data is communicated and stored on the tag 300 by the pharmaceutical company computer system 102 during the manufacture/packaging of the medication. The medication data 126 may include information relating to the manufacture of the corresponding medication, e.g., manufacturing date, batch/lot number, manufacturing location, authenticity information (anti-counterfeiting data), expiration date, name of medication, packaging information, and the like.

The memory 304 further includes prescription data 128 communicated to the tag 300 via the pharmacy computer system 160 at the point of delivery of the medication package 150 to the patient/user. In one embodiment, the prescription data 128 may include, for example and without limitation, dosage information, frequency of use information, prescribing clinician, pharmacist information, pharmacy information, refill information, emergency contact information (poison control, medication interactions, etc.). As part of the prescription data 128, or the medication data 126, information related to drug interactions, overdose concerns, impairment information, and the like, may also be stored in the memory 304 of the tag. Other incidental information relating to the medication may also be included in the memory 304 via the prescription data 126 and/or the prescription data 128, including legal information, disclaimers, ingredient lists, active/inactive ingredient identification information, and the like.

In addition, the memory 304 may store patient data 130 corresponding to the patient to whom the prescription and medication is directed. For example, the patient data 130 may include name, age, gender, allergies, conditions, insurance information, and other relevant medical/patient information as will be appreciated by those skilled in the art. The transceiver 306 of the tag 300 may correspond to any suitable component capable of establishing bi-directional communication between the tag 300, the pharmaceutical company computer system 102, the pharmacy computer system 160, and the user device 400.

In accordance with one embodiment, the tag 300 contains specific information stored by the pharmacist before delivering the medication (e.g. medication details, patient age and gender, prescription details). In such an embodiment, a best means to protect this information is to encrypt it with a proper mechanism. Accordingly, the embodiments contemplated herein utilize implementation of encryption using a Public Key Infrastructure: the pharmacy computer system 160 has access to the public key 120 of the infrastructure (i.e., the pharmaceutical company computer system 102), and can use the public key 120 to encrypt data. And this data can only be decrypted with the private key 122, which is controlled by the pharmaceutical company computer system 102. Thus, provided that the encryption scheme is strong enough, e.g., RSA 2048, getting access to the data 126, 128, 130, etc., stored in the memory 304 of the tag 300 will be useless to an attacker who do not have the private key 122. The tag 300 may be implemented as a READ-ONLY tag, whereupon after data 126-130 is written to the tag 300 by the pharmacy computer system 160, it cannot be tampered with or altered once possession of the medication package 150 has passed to the patient.

It will be appreciated that the application of the tag 300 to the medication package 150 can assist in the detection of counterfeit medication. As will be understood, the tag 300 can have a digital signature (e.g., medication data 126 signed via private tag 122 by pharmaceutical company computer system 102) added to the tag 300 at build time. The digital signature can be made using the aforementioned public key infrastructure (public key 120/private key 122), and encrypting, using the private key 122, a unique identifier, batch number, expiration date, or other available data. When the tag 300 is read by the pharmacy computer system 160, the pharmacy application 152 can check the validity of such a signature with the public key 120, and immediately detect counterfeit drugs when the signature does not match.

Returning to FIG. 2, the system 100 further includes an exemplary pharmacy computer system 160 in communication with the pharmaceutical company computer system 102 via a suitable network, e.g., the Internet 101, as discussed below. The pharmacy computer system 160 may be configured to interact with the medical package 150, i.e., the tag 300, as well as the user device 400, as are illustrated therein. The pharmacy computer system 160 includes a processor 162, which performs portions of the exemplary method by execution of the pharmacy application 152 that is stored in memory 164 connected to the processor 162, as well as controlling the overall operation of the pharmacy computer system 160. It may be appreciated that the pharmacy computer system 160 may be implemented as a specific device configured to interact/communicate with the tag 300, a set of connected components (as illustrated) configured to interact with the pharmaceutical company computer system 102, the Internet 101, the tag 300, the user device 400, and other devices or entities (not shown). In some embodiments, the pharmacy computer system 160 may be function similar to that of a point-of-sale terminal, as are commonly utilized in pharmacies. As shown in FIG. 2, the pharmacy computer system 160 includes a short-range communications transceiver 176 coupled to the bus 166 and in communication with the processor 162. In one embodiment, the transceiver 176 is a Near Field Communications ("NFC") transceiver, configured to communicate with tags 300 or other NFC-equipped devices, e.g., the user device 400.

The pharmacy application 152 includes an encryption/decryption module 178 that utilizes public key encryption (PKI) in the form of a public key 120 and a private key 122 pair for secure communications and authentication purposes. According to one embodiment, the encryption/decryption module 178 is configured to utilize the private key 122 received from the pharmaceutical company computer system 102 during installation of the application 152 to encrypt patient data 128 and prescription data 130 for subsequent storage thereof on the tag 300 affixed to the medication package 150 provided by the pharmacy to the user in accordance with the prescription being filled. The public key 120 may be utilized by the encryption/decryption module 178 to decrypt medication data 126 stored on the tag 300. It will be appreciated that some embodiments contemplated herein provide for storage by the pharmacy computer system 160 for confirmation that the appropriate medication was dispensed, in case a patient returns with questions, refills, and myriad other purposes related to pharmacy operations.

The pharmacy application 152 may also include a data collection module 180 configured to collect, via direct communication (electronic medical record/correspondence from prescribing doctor), or via a graphical user interface using patient/pharmacist input, prescription data 128, patient data 130, and the like. In accordance with one embodiment, the data collection module 180 is configured to collect patient data 130, prescription data 128, medication data 126, and the like during interactions with the patient/user and the medication package 150. It will be appreciated that the patient data 130 and prescription data 128 may be input via a graphical user interface on the display 172 of the pharmacy computer system 160 using the various input devices 174 by the pharmacist, may be collected via the data collection module 180 during electronic communication from the prescribing authority (e.g., doctor, etc.), or the like. In other embodiments, the data collection module 180 may work in conjunction with the encryption/decryption module 178 to collect medication data 126 from the tag 300 and decrypt the same. Other cooperation includes, for example, communication of collected data (patient data 130, prescription data 128, etc.) by the collection module 180 to the encryption/decryption module 178 for encryption and subsequent writing thereof to the memory 304 of the tag 300.

As shown in FIG. 2, the pharmacy computer system 160, via execution of the pharmacy application 164, establishes a NFC communications link 192 with the tag 300 affixed to the medication package 150. In accordance with one embodiment, the pharmacist (not shown) will select the appropriate medication package 150 corresponding to a prescription submitted by a user or received electronically from a prescribing authority, e.g., medical doctor, dentist, etc. The package 150 is then brought into relative proximity to the transceiver 176 associated with the pharmacy computer system 160, depending upon the type of tag 300 utilized by the package 150, the distance between the tag 300 and transceiver 176 will accordingly vary, as will be appreciated by those skilled in the art. Once an NFC link 192 has been established, the pharmacy computer 160, via the application 152, collects patient data 130, prescription data 128, and medication data 126 via the data collection module 180. The application 152 includes the private key 122, enabling encryption of the patient data 130 and prescription data 128 by the encryption/decryption module 178, and the public key 120, enabling the decryption (via module 178) of medication data 126 of the tag. In one embodiment, the keys 120-122 are received by the pharmacy computer 160 from the pharmaceutical company computer system 102 during downloading of the pharmacy application 152 and/or registration of the computer 160. The encrypted data (patient data 130 and prescription data 128) is then written onto the tag 300. The medication package 150 is then provided to the user by the pharmacist. Further interactions between the pharmacy computer 160 and the tag 300 are illustrated below with respect to FIG. 7.

The system 100 depicted in FIG. 2 further includes at least one user device 400 is shown in communication with the tag 300 and the pharmaceutical company computer system 102 via respective communication links 188 and 190. That is, the user device 400 may utilize a communications link 188 with the pharmaceutical company computer system 102, which allows access to a secure URL 132 hosted by the system 102 for receiving information regarding medications and for reporting side effects and/or user feedback 156. In one embodiment, the user device 400 may be implemented as a smartphone employing an operating system such as iOS, ANDROID, BLACKBERRY, WINDOWS, or the like. The user device 400 is representative of any personal computing devices, such as personal computers, netbook computers, laptop computers, workstation computers, personal data assistants, web-enabled cellular telephones, tablet computers, proprietary network devices, or other web-enabled electronic devices. The data communications link 188 between the user device 400 and the pharmaceutical company computer system 102 may be accomplished via any suitable channel of data communications such as wireless communications, for example Bluetooth, WiMax, 802.11a, 802.11b, 802.11g, 802.11(x), a proprietary communications network, infrared, optical, the public switched telephone network, or any suitable wireless data transmission system, or wired communications. In one embodiment, the user device 400 may communicate with the pharmaceutical company computer system 102 via the Internet 101.

Figure 4:
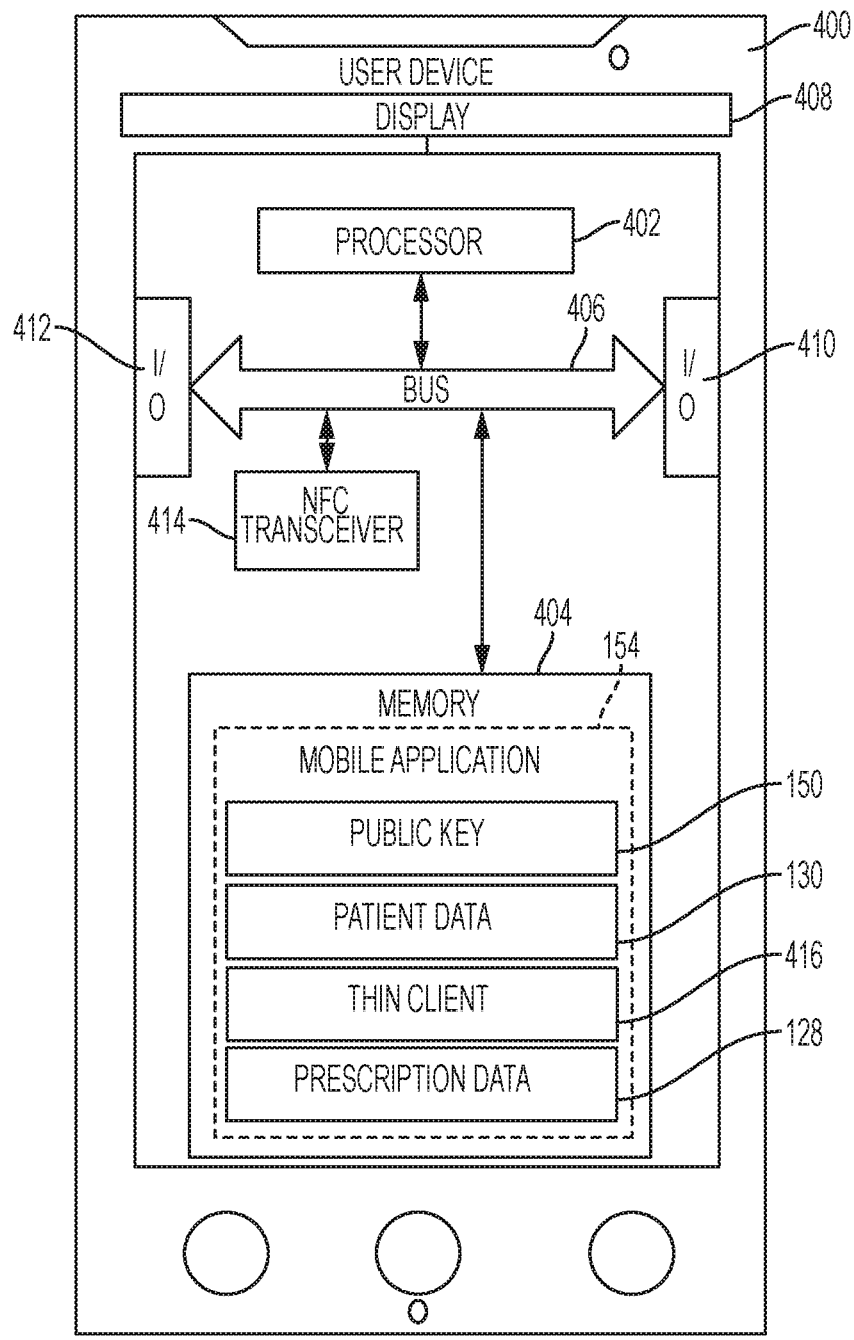
FIG. 4 is a functional block diagram of a user device for use in the NFC-enabled medication packaging bi-directional communication system in accordance with one embodiment of the subject application.

FIG. 4 provides an example illustration of a user device 400 representative of the user device depicted in FIG. 1. The user device 400 may include a processor 402, which executes one or more instructions or applications 154 in the performance of an exemplary method discussed below. The user device 400 may further include a memory 404 storing the application 154 in data communication with the processor 402 via a system bus 406. The processor 402 of the user device 400 may be in data communication with the pharmaceutical company computer system 102 via an I/O interface 412 and the tag 300 via an I/O interface 410. In one embodiment, the I/O interface 410 is implemented as a short-range communication component, such as, for example an NFC transceiver 414. In such an embodiment, the I/O interface 410 utilizing the NFC transceiver 414 may be configured to provide power to the tag 300 to enable communication there between. In other embodiments, the short range communication component 414 may be implemented using any suitable short range communications protocol, and the use of NFC protocols is for example purposes only. The user device 400 may further include a display 408 suitably configured to display data to an associated user, receive input from the associated user, and the like. In some embodiments, the display 408 of the user device 400 may be configured as a touch-screen display capable of receiving user instructions via user contact on the display, e.g., LCD, AMOLED, LED, RETINA, etc., types of touch-screen displays. For example, the display 408 may be capable of displaying medication information, feedback questionnaires, patient information 130, a thin client 416 (e.g., web-enabled browser), a graphical user interface associated with the mobile application 154, and the like.

The memory 404 may represent any type of non-transitory computer readable medium such as random access memory (RAM), read only memory (ROM), magnetic disk or tape, optical disk, flash memory, or holographic memory. In one embodiment, the memory 404 comprises a combination of random access memory and read only memory. In some embodiments, the processor 402 and memory 404 may be combined in a single chip. The network interface(s) 410, 412 allow the user device 400 to communicate with other devices via a communications network, and may comprise a modulator/demodulator (MODEM). Memory 404 may store data the processed in the method as well as the instructions for performing the exemplary method. The digital processor 402 can be variously embodied, such as by a single core processor, a dual core processor (or more generally by a multiple core processor), a digital processor and cooperating math coprocessor, a digital controller, or the like.

The memory 404 of the user device 400 includes the application 154, which may include the public key 150 for decrypting information received from the pharmaceutical company computer system 102 or tag 300. The user device 400 may be configured to further store the patient data 130 in memory in conjunction with the application 154. In addition, the memory 404 may store a thin client 416, as discussed above, enabling the mobile device 300 to communicate with the pharmaceutical company computer system 102 via the secure URL 132, as discussed herein.

As will be appreciated, the application 154 collects the data 126, 128, 130 from the tag 300, as well as other data about the user, e.g., email address, feedback 156, and the like. In accordance with one embodiment, the prescription data 128 and patient data 130 from the tag 300 is encrypted, such that the application 154 is incapable of decoding it. Thus, as will be appreciated, additional security is not needed in some embodiments set forth herein. Furthermore, the email address and the other personal information/data collected via the application 154 may utilize the standard mechanisms proposed/used by the mobile platforms (e.g., iOS, ANDROID, MICROSOFT, BLACKBERRY, etc.), which already store the same kinds of data. Any additional data, e.g., feedback data 156, need not necessarily be stored on the user device 400, and can reside in memory 404 temporarily prior to be communicated to the pharmaceutical company computer system 102, as discussed in greater detail below.

As shown in FIG. 1, the user device 400 is capable of intermittent (opportunistic) or continuous bi-directional communication with the pharmaceutical company computer system 102 utilizing the I/O interface 412. In one embodiment, the bi-directional communication is data communication utilizing a cellular data network, e.g., $3^{rd}$ generation mobile phone standards (3G), $4^{th}$ generation standards (4G, 4G LTE, WiMax), EV-DO, standalone data protocols, and the like. In such an embodiment, the user device 400 communicates with the pharmaceutical company computer system 102 using the Internet 101. The user device 400 may provide patient data 130 to the pharmaceutical company computer system 102. The pharmaceutical company computer system 102 may then send alerts, queries, medication information, and the like, to the user device 400 for display to the patient.

The user may bring the user device 400 into proximity with the tag 300 affixed to the medication package 150 to retrieve medication information 126 stored in memory 304, as well as the corresponding secure URL 132. Once in proximity, the I/O interface 410, i.e., the NFC component 414 of the user device 400, may generate an RF field which is capable of powering the tag 300. The user device 400 then reads the tag 300 (establishes an NFC radio communication link 190 with the tag 300). The processor 402, in accordance with the application 154, then retrieves the medication data 126 with secure URL 132, the encrypted prescription data 128, and the encrypted patient data 130 from the tag 300.

The application 154 being executed by the processor 402 may then result in a display of the medication data 126 on the user device display 408 to the user. The processor 402 may then initiate a thin client interface 416, e.g., a web browser, of the user device 400 to open the secure URL 132 read from the memory 304 of the tag 300. The secure URL 132, as discuss supra, may correspond to a secure website hosted by the pharmaceutical company computer system 102, configured to communicate with the user of the user device 400 for the exchange of information. Once connected to the pharmaceutical company computer system 102, the user device 400, via application 154, communicates the encrypted patient data 130 and prescription data 128, thereby ensuring that any interceptions of the data 128-130 will not result in compromising the security of the personal information contained therein, i.e., only devices having the private key 122 will be able to decrypt the encrypted data, e.g., the pharmaceutical company computer system 102. According to on embodiment, the thin client 416 may facilitate the communication of feedback 156 to the pharmaceutical company computer system 102 via the secure URL 132, such as side effects, dosage issues, and the like. In addition, varying embodiments contemplated herein may utilize the application 154 on the user device 400 to alert the user as to side effects, prompts to take the medication, and the like, whereupon the user device 400 may emit a sound, vibration, graphical indicia, or the like corresponding to the aforementioned alert. Further operations of the user device 400 will be better understood in conjunction with the methodology illustrated in FIG. 8, discussed below.

Figure 5:
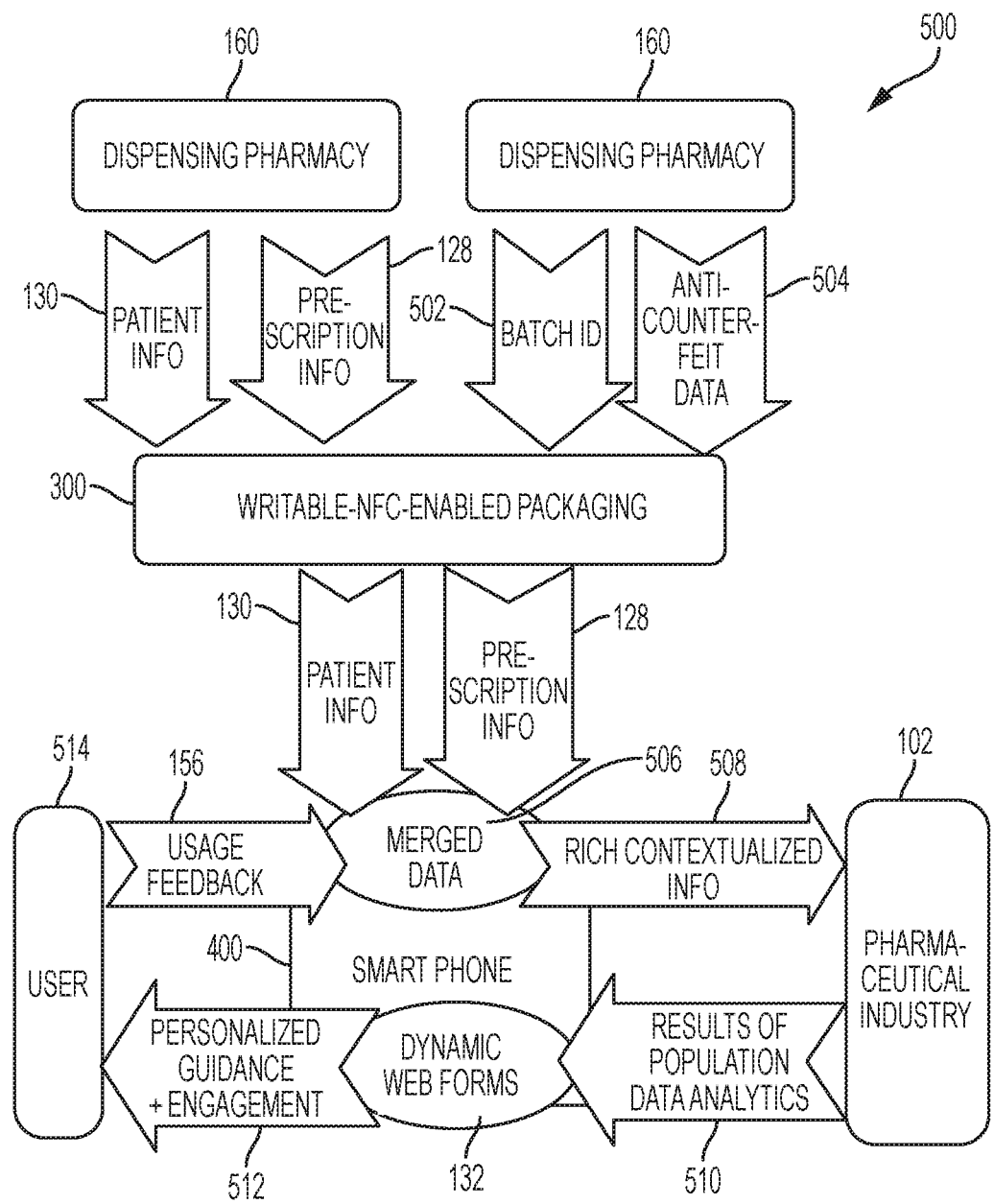
FIG. 5 is a functional block diagram illustrating interactions of the various components of the NFC-enabled medication packaging bi-directional communication system according to one embodiment of the subject application.

Referring now to FIG. 5, there is shown a functional block diagram 500 illustrating interactions of the various components of the NFC-enabled medication packaging system for bi-directional communication between a patient's user device 400 and the pharmaceutical company computer system 102 in accordance with one example implementation of the subject application. As shown in FIG. 5, an NFC tag 300 is added to a medical packaging 150, either at build time, or later in the process. For example, as briefly described supra, the tag 300 can be integrated in the ply of the packaging 150, or affixed to the outside, e.g., a self-adhesive component in which the tag 300 is embedded. The tag 300 is initialized via the initialization module 110 with medication data 126 (name, packaging, batch number 502, expiration date, etc.) and a digital signature (e.g., for authentication, as discussed below).

Prior to dispensing the medication to the patient, the pharmacist collects relevant information about the patient: age, gender, which might be already available in the customer record (i.e., the prescription data 126), and prescription details (i.e., the prescription data 128). It will be appreciated that the prescription data 128 may need to be manually entered in the pharmacy computer system 160, or may already be available in the case of an electronic prescription. In some embodiments, the prescription data 128 may not be available, depending upon, for example and without limitation, privacy policies, time required to enter the information, and the like.

According to the diagram 500 of FIG. 5, the pharmacist taps the medicine package 150 to an NFC device (i.e., the transceiver 176) connected to the pharmacy computer system 160, e.g., a Point of Sale (POS) computer. While tapping, an NFC connection 192 is established between the tag 300 on the package 150 and the tag writer, i.e., the transceiver 176 of the pharmacy computer system 160. Medication data 126 (e.g., name, packaging, batch number 502, expiration date, etc.) and digital signature (e.g., anti-counterfeiting data 504) is read from the NFC tag 300 on the package 150 by the pharmacy computer system 160.

The pharmacy computer system 160, via the encryption/decryption module 178, verifies the authenticity of the digital signature, e.g., the anti-counterfeiting data 504, to detect potential counterfeit products, then encrypts (as previously discussed) the patient data 130, prescription data 128, and medication data 126, and writes the encrypted data to the NFC tag 300. The medicine package 150 accordingly now has an NFC tag 300 containing relevant information about the medication, the patient, and the prescription.

Thus, each time the patient taps the user device 400, i.e., their smartphone or other NFC-enabled personal computing device, on the medicine package 150, the user device 400 displays personalized guidance 512 about the treatment and allows the patient to send feedback 156 to the pharmaceutical company computer system 102 that will be received with all relevant context. By tapping the user device 400 on the medicine package 150, the patient is also able to check the authenticity of the medication, as the application 154 will verify the digital signature, i.e., the anti-counterfeiting data 504, embedded in the tag 300 to detect potential counterfeit.

From the perspective of the user device 400, i.e., a patient's mobile phone, in FIG. 5, the systems and methods recited herein provide several implementation options, of which two non-limiting, exemplary embodiments are described hereinafter. First, through a dedicated application 154 that the user will need to install on the user device 400. It will be understood that this implementation provides substantial functionality, but requires the user to have installed the aforementioned dedicated application 154 on user device 400, i.e., their phone, prior to accessing the medication data 126 and other information stored on the tag 300. In particular, the application 154 can collect additional information about the patient, both automatically (e.g. email address), or manually. Second, the tap, i.e., the NFC communications link 190, directly opens a web browser, i.e., the thin client interface 416, pointing to the relevant page (e.g., the secure URL 132) on the pharmaceutical company computer system 102. It will be appreciated that this second exemplary embodiment is simpler than the first, as most user devices 400 (i.e. smart phones) include native web browsers, but offers less customization. Furthermore, a combination of these implementations may be utilized as illustrated in greater detail above.

In accordance with one embodiment, when it is not possible to initialize the NFC tag 300 with medication data 126 at the time of manufacture, the medication data 126 should be available in a barcode or QR code on the medication packaging 150. In this case, the pharmacist needs to scan the medication packaging 150 barcode or QR code to collect this information from the pharmaceutical company computer system 102 or deciphered from the barcode or QR code before tapping the NFC tag 300 to establish the NFC link 192 therebetween, whereupon the pharmacy computer system 160 is tasked with writing the medication data 126 (and corresponding anti-counterfeiting data 504) to the memory 304 of the tag 300.

Figure 6:
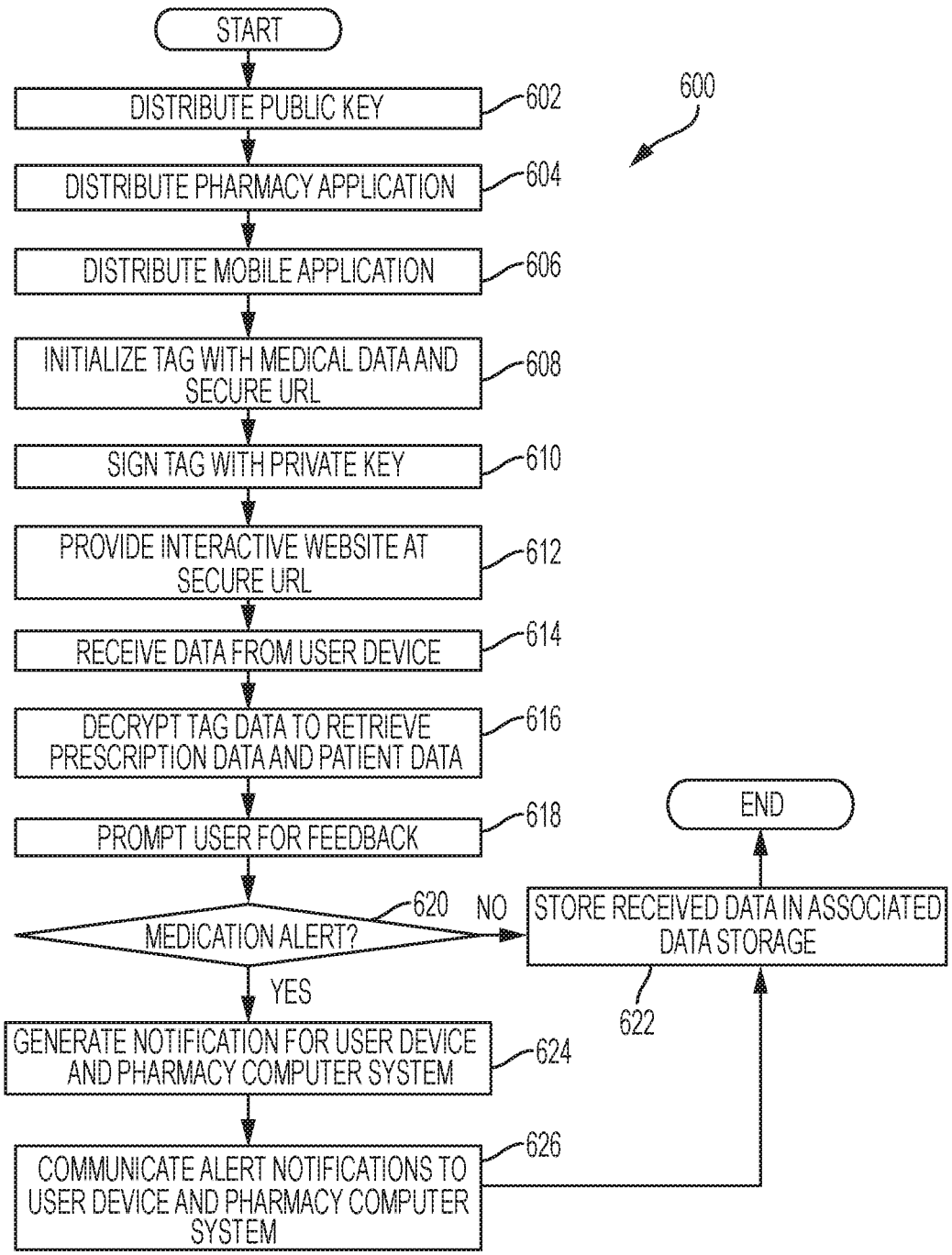
FIG. 6 is a flowchart illustrating an exemplary method for NFC-enabled medication packaging bi-directional communications employed by a pharmaceutical company computer system in accordance with one embodiment of the subject application.
Figure 11:
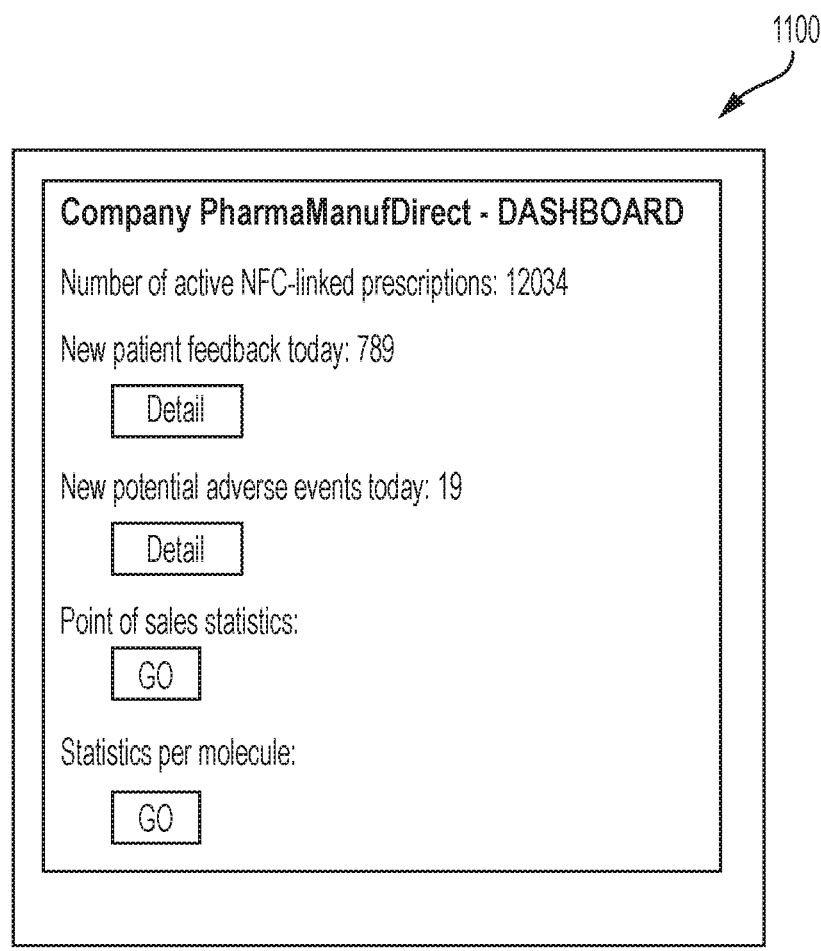
FIG. 11 is an example graphical user interface displayed on a pharmaceutical company computer system in the NFC-enabled medication packaging bi-directional communication system in accordance with one embodiment of the subject application.

Turning now to FIG. 6, there is shown an exemplary flowchart 600 illustrating operations of the pharmaceutical company computer system 102 in accordance with one embodiment of the subject application. An exemplary graphical user interface 1100 is depicted in FIG. 11 showing user interactions with respect to the pharmaceutical company computer system 102 in accordance with some embodiments disclosed herein. Beginning at 602, the pharmaceutical company computer system 102 distributes or otherwise makes the public key 120 available, enabling decryption and/or authentication of communications by the system 102 available. In some embodiments, the public key 120 is made available via incorporation thereof in an application 152, 154, via direct downloading, direct communication, or the like. At 604, the pharmaceutical company computer system 102 distributes or otherwise makes the pharmacy application 152 available for downloading by the pharmacy computer system 160. In some embodiments, the pharmaceutical company computer system 102 facilitates the distribution of the application 152 to various pharmacies dispensing the medicine produced by the company, publishes the application 152 to a suitable distribution partner, e.g., ITUNES, GOOGLE PLAY, or other source.

At 606, the mobile application 154 is distributed to user devices 400 via a suitable network, e.g., ITUNES, GOOGLE PLAY, AMAZON APP STORE, and the like. It will be appreciated that the mobile application 154 may be distributed to user devices 400 via links to the secure URL 132, available for download from the pharmaceutical company computer system 102, or other methods of distributing an application on a user device. In some embodiments, the application 154 is made available via direct communication from the pharmacy computer system 160 when a patient arrives to pick up a prescription. At 608, the pharmaceutical company computer system 102 initializes the tag 300 with medical data 126 and the secure URL 132. It will be appreciated, as explained in greater detail above, that the tag 300 may be affixed to the exterior of the medicine package 150 or embedded within the package 150 itself. As addressed above, the tag 300 may receive medication data 126 (e.g., name, packaging, batch number 502, expiration date, etc.) and digital signature (e.g., anti-counterfeiting data 504) from the pharmaceutical company computer system 102 at 608. At 610, the aforementioned medication data 126 is signed by the pharmaceutical company computer system 102 using the private encryption key 122, thereby generating suitable anti-counterfeiting data 504, which is stored in memory 304 of the tag 300. The pharmaceutical company computer system 102 then publishes, at 612, a website at the secure URL 132 for access by a user device 400.

At 614, data is received from the user device 400, which includes, for example and without limitation, medication data 126, prescription data 128, and patient data 130 via the interaction module 114 of the pharmaceutical company computer system 102. In accordance with one embodiment, the data 126-130 is received via network connections 188 and 149 utilizing a secure medium of exchange, as discussed above. To ensure security, it will be appreciated that the application 154 resident on the user device 400 may encrypt the data 126-130 using the public key 120 (where applicable). Alternatively, the user device 400 may communicate encrypted data 126-130 retrieved from the tag 300, in essence functioning as an intermediary between the medication package 150 and the pharmaceutical company computer system 102. In such an implementation, the user device 400 does not gain access to unencrypted data 126-130, instead merely forwarding this information on to the pharmaceutical company computer system 102. As addressed above, the data 126-130 may be received by the pharmaceutical company computer system 102 via a secure URL 132, i.e., a secure (https) web site to which the user device 400 accesses.

The data 126-130 is then decrypted, at 616, via the encryption/decryption module 112 using the private key 122 from data storage 144 by the pharmaceutical company computer system 102. In one embodiment, subsequent to decrypting the aforementioned data and optionally creating a patient account, the analysis module 116 analyzes the data and in concert with the interaction module 114, prompts the user via the display 408 of the user device 400 for user feedback 156 at 618. As indicated above with respect to FIG. 5, the prompt to the user device 400 may include customized and personalized information regarding the medication, the patient's experience with the medication, side effects, and other information.

At 620, a determination is made whether a medication alert is to be generated and reported to a patient via the analysis module 116 and notification module 118. Upon a negative determination at 620, operations proceed to 622, whereupon the received, decrypted data 126-130 is stored in the associated data storage 144. Upon a determination at 620 that a medication alert is available, operations progress to 624, whereupon the notification module 118 generates an alert notification for the user device 400 and the pharmacy computer system 160. The alert notification is then communicated, at 626, to the user device 400 associated with the corresponding medication and the pharmacy computer system 160. Operations then proceed to 622 for storage of the decrypted data 126-130 on the associated data storage 144.

Figure 7:
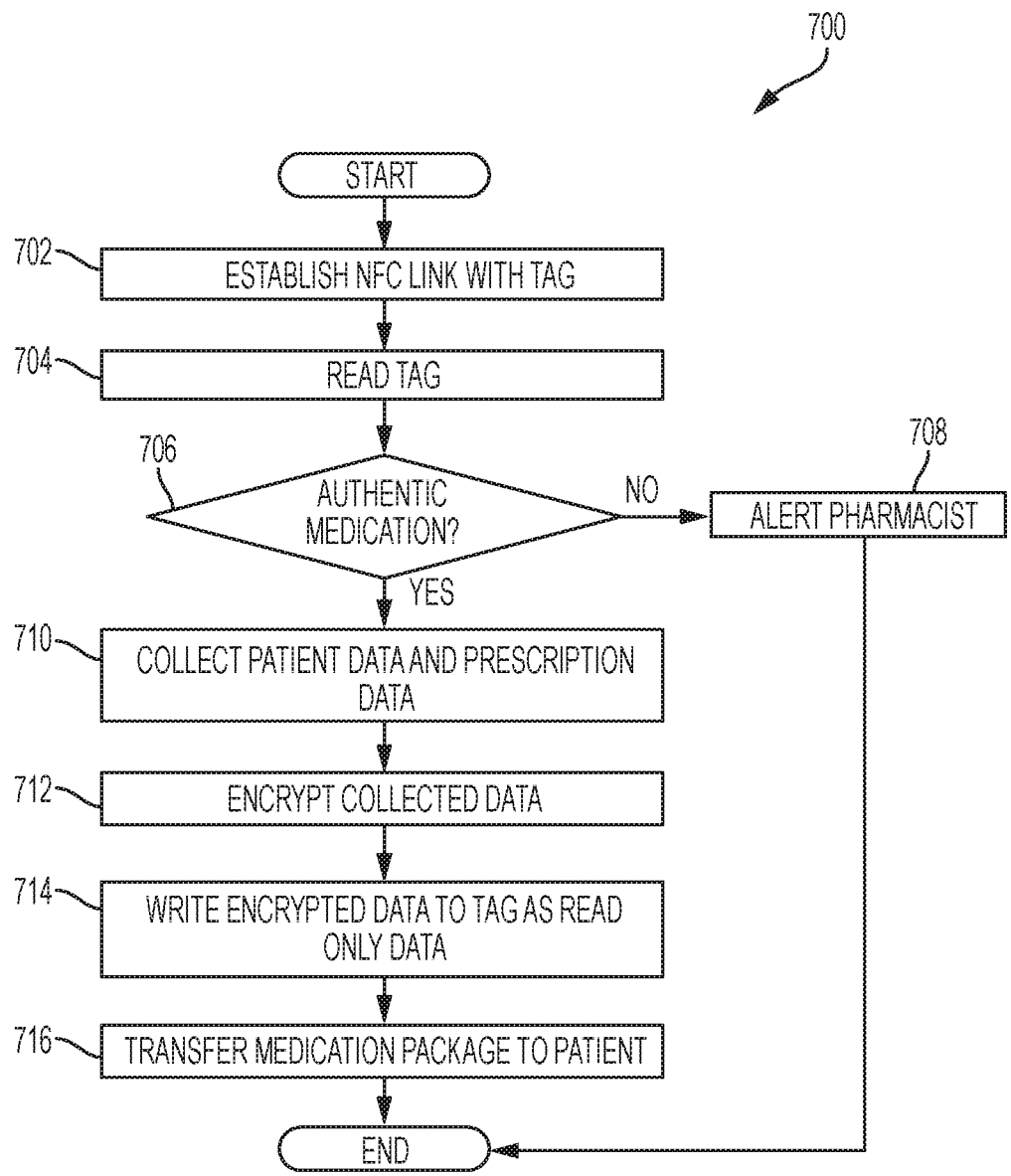
FIG. 7 is a flowchart illustrating an exemplary method for NFC-enabled medication packaging bi-directional communications employed by a pharmacy computer system in accordance with one embodiment of the subject application.

Referring now to FIG. 7, there is shown an exemplary flowchart 700 illustrating operations of the pharmacy computer system 160 in accordance with one embodiment of the subject application. It will be understood that the operations depicted in FIG. 7 occur after the pharmacist or pharmacy technician has received a prescription (in paper, via telephone/facsimile, or electronically), and has selected the medication package 150 corresponding to the medication identified in the associated prescription. The pharmacist or technician then enters (if manually required) the available patient data 130, the prescription data 128, and if necessary, utilizes the pharmacy computer system 160 to retrieve the medication data 126 from the pharmaceutical company computer system 102. Accordingly, at 702, the pharmacy computer system 160, via the NFC transceiver 176, establishes a NFC link 192 with the tag 300 affixed/embedded/corresponding to the medication package 150 containing the prescribed medication.

At 704, the pharmacy computer system 160, via the transceiver 176, reads the memory 304 of the tag 300. The pharmacy computer system 160 retrieves the medication data 126 (if applicable) and anti-counterfeiting data 504 (i.e., the digital signature) from the memory 304 and determines, at 706, whether the medication package 150, i.e., the medication, is authentic. That is, the pharmacy computer system 160 decrypts the signed anti-counterfeiting data 504 using the available key (public key 120/private key 122, depending upon which key is present on the system 160). If the data 504 is validated via the key 120 or 122, the pharmacy computer system 160 identifies the medication as authenticate, whereas an invalid result is indicative of unauthorized or non-authentic medication. Upon a determination that the medication is not authentic, operations proceed to 708, whereupon an alert, i.e., graphical indicia via the display 172 and/or audible alert, is generated notifying the pharmacist of the non-authentic medication.

Figure 10:
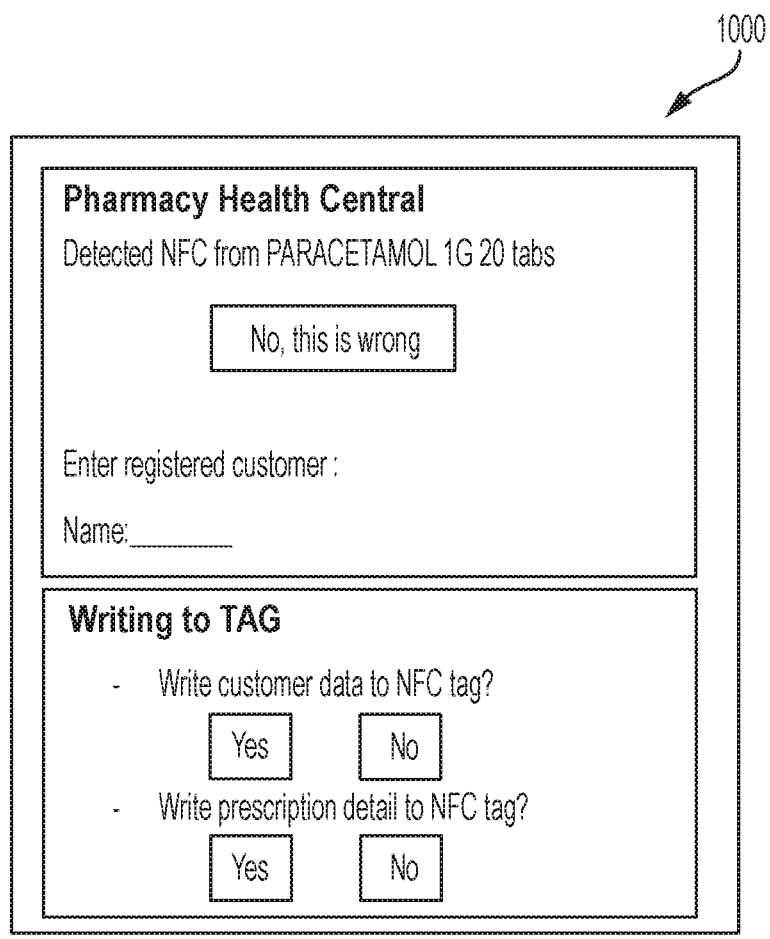
FIG. 10 is an example graphical user interface displayed on a pharmacy computer system in the NFC-enabled medication packaging bi-directional communication system in accordance with one embodiment of the subject application.

Upon a determination at 706 that the medication package 150 is authentic, operations proceed to 710. At 710, the collection module 180 or other suitable component associated with the pharmacy computer system 160 collects the prescription data 128, the patient data 130 for encryption by the encryption module 178 at 712. After encryption, operations proceed to 714, whereupon the encrypted data 128-130 is written to the memory 304 of the tag 300 associated with the medication package 150 containing the patient's prescription. Preferably, the data 128-130 is encrypted using the appropriate key 120 or 122 (depending on the keys available to the pharmacy computer system 160), thereby ensuring that only the pharmaceutical company computer system 102 will be able to decrypt and analyze the data. The writing to the tag 300, as will be appreciated, may be performed such that the data 128-130 as read-only, thereby preventing modification by the user device 400 or other device. FIG. 10 provides a graphical user interface 1000 illustrating interactions between a pharmacist/technician of the pharmacy computer system 160 and the tag 300, enabling identification of the tag 300, as well as writing patient data 130 and prescription data 128 to the tag 300, as discussed above. Thereafter, the medication package 150, with the tag 300 containing the encrypted data 128-130, is transferred to the patient.

Figure 8:
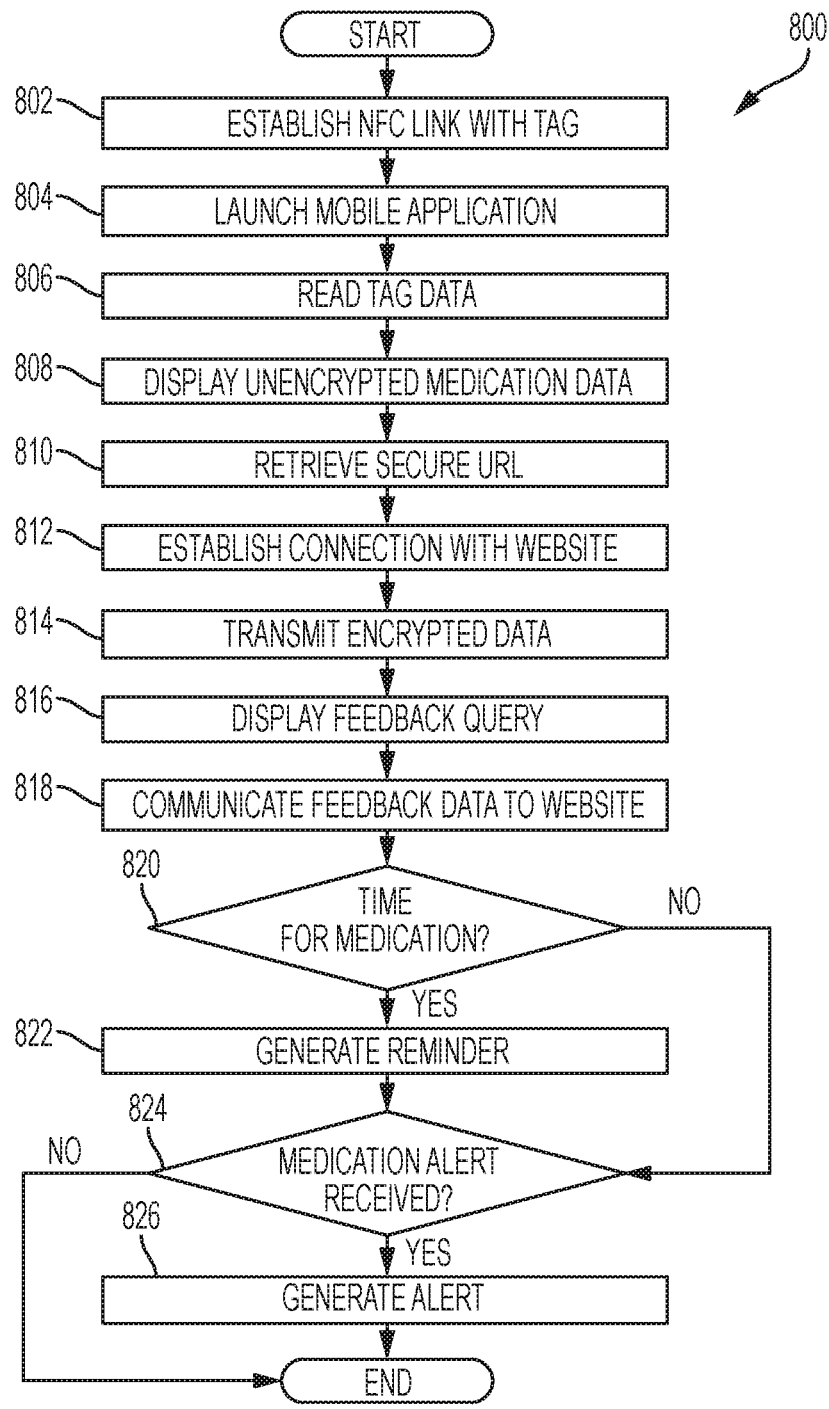
FIG. 8 is a flowchart illustrating an exemplary method for NFC-enabled medication packaging bi-directional communications employed by a user device in accordance with one embodiment of the subject application.

FIG. 8 depicts a flowchart 800 illustrating operations of the user device 400 in accordance with one embodiment of the subject application. It will be appreciated that the methodology depicted in FIG. 8 occurs subsequent to the patient receiving the medication package 150 from the pharmacist and after installation of the application 154 in memory 404 of the user device 400. Accordingly, at 402, an NFC communication link 190 is established between the user device 400 and the tag 300 of the medication package 150. It will be understood that the establishment of the communication link 190 occurs using the NFC standard promulgated by the IEEE, e.g., the user device 400 is brought into relative proximity with the tag 300. At 804, the application 154 is launched in response to the establishment of the NFC link 190 on the user device 400.

Figure 9:
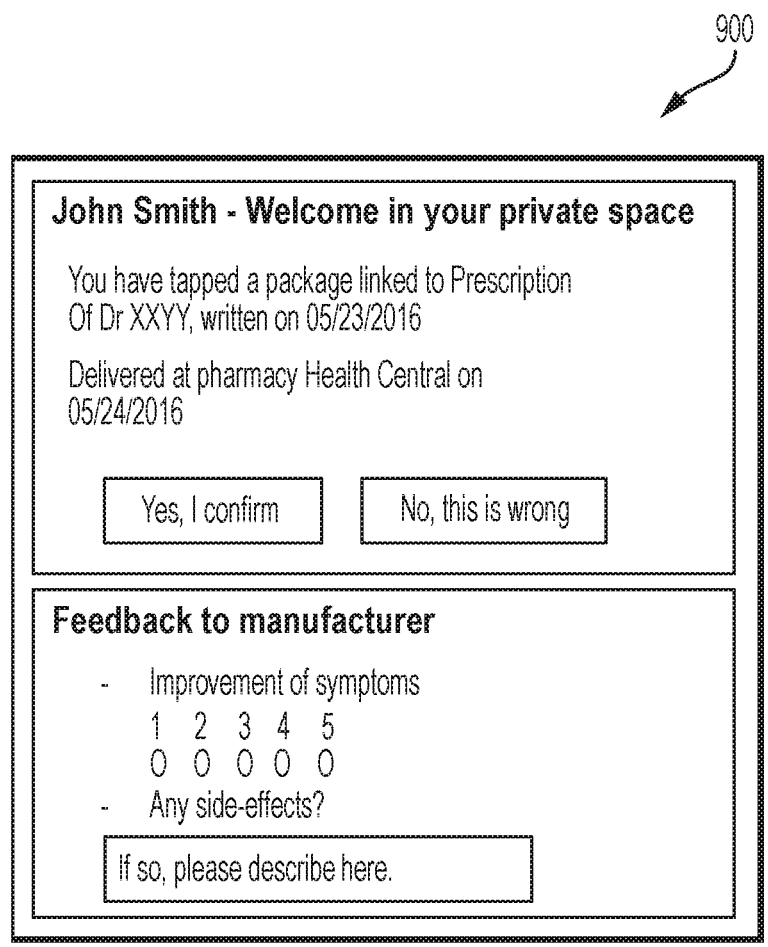
FIG. 9 is an example graphical user interface displayed on a user device in the NFC-enabled medication packaging bi-directional communication system in accordance with one embodiment of the subject application.

Data, e.g., the medication data 126, prescription data 128, patient data 130, etc., is read from the memory 304 of the tag 300 by the user device 400 at 806. It will be appreciated that the user device 400 does not have access to either the public key 120 or the private key 122, thereby preventing the user of the user device 400 from modifying or otherwise discerning the encrypted prescription data 128 and patient data 130. At 808, the medication data 126 retrieved from the tag 300 is displayed on the user device 400 via the associated display 408. As previously indicated, the medication data 126 includes a secure URL 132 for establishing direct communications between the user device 400 and the pharmaceutical company computer system 102. Thus, at 810, the secure URL 132 is determined from the retrieved medication data 126 by the processor 402 or other suitable component of the user device 400. FIG. 9 provides an illustration of a graphical user interface 900 displayed on the display 408 of the user device 400 responsive to the establishment of the aforementioned communications link 190. As depicted in FIG. 9, the graphical user interface 900 provides the patient/user of the user device 400 with relevant information relating to the medication package 150, retrieved from the tag 300. The graphical user interface 900, as discussed in greater detail below, further provides prompts to the user soliciting feedback 156 regarding the efficacy of the medication as well as the side effects (if any) associated therewith.

A connection 188 is then established between the application 154 or thin client 416 of the user device 400 and the website designated by the secure URL 132 hosted by the pharmaceutical company computer system 102 at 812. It will be understood that direct communications via the application 154 and a secure link (not shown) may also be utilized when available between the user device 400 and the pharmaceutical company computer system 102. The encrypted data 128 and 130 are then communicated from the user device 400 to the pharmaceutical company computer system 102 at 814.

At 816, the mobile application 154 utilizing the display 408, generates a graphical user interface thereon displaying a feedback query received from the pharmaceutical company computer system 102. In some embodiments, the query may comprise personalized guidance and engagement information 512, dynamic web forms 132, the results of population data analytics 510, and the like. The feedback 156 is then communicated from the user device 400 to the pharmaceutical company computer system 102 at 818. As will be appreciated, the feedback data 156 may be encrypted via the public key 120 by the user device 400, or communicated via https and the secure URL 132, or a combination of both, ensuring user privacy.

The mobile application 154, via the processor 402 or other suitable component associated with the user device 400 then determines, at 820, whether it is time for the patient to take the medication. It will be understood that this optional step may be set up by the user, preset up with the prescription data 128/medication data 126, set up by the pharmacy computer system 160, or received from the pharmaceutical company computer system 102 after the secure communications between the system 102 and the user device 400 have been established. Upon a positive determination at 820, operations proceed to 822, whereupon a prompt is generated on the display 408 of the user device 400 indicating the need to take the medication, e.g., graphical indicia, sound, vibration, or a suitable combination thereof.

After prompting the user at 822, or upon a negative determination at 820, operations proceed to 824, whereupon a determination is made whether a medication alert has been received from the pharmaceutical company computer system 102. In the event that a medication alert, i.e., a newly discovered drug side effect, interaction, counter-indication, etc., is available, operations proceed to 826, whereupon an alert is generated on the display 408 of the user device 400 indicating the aforementioned alert, e.g., graphical indicia, sound, vibration, or a suitable combination thereof. Returning to 824, upon a determination that no medication alert has been received from the pharmaceutical company computer system 102, operations with respect to FIG. 8 terminate.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A near-field communication (NFC)-enabled medication packaging system, comprising:
 a server associated with a pharmaceutical company, comprising:
  a processor in communication with memory;
  a near-field communications transceiver in data communication with the processor and memory; and
  a data storage in communication with the processor, the data storage storing a public key and a private key;
  wherein the memory stores instructions which are executed by the processor to:
   initialize a tag of a medicine package with medication data corresponding to a medication contained therein, wherein the tag of the medicine package is configured as an NFC-enabled, write-only tag affixed to the medicine package, the tag including a tag memory storing medicine data, prescription data, and patient data and wherein initializing the tag further comprises writing each of a medication name, a medication packaging, a batch number, and an expiration date on the tag via an NFC communications link,
   sign the tag using the private key to establish authentication of the medication contained in the medicine package,
   receive encrypted data from a user device of an associated patient via a secure communications link over a computer network, the encrypted data including feedback data representative of a use of the medication by the patient and at least one of prescription data and patient data,
   decrypt the received encrypted data to retrieve the feedback data and the at least one of the prescription data and the patient data,
   analyze the retrieved feedback data,
   generate personalized guidance specific to the patient in accordance with the analyzed feedback data and at least one of the prescription data and the patient data, and
   communicate, via the secure communications link over the computer network, the personalized guidance specific to the patient to the user device; and
 a pharmacy computer separate from the server, the pharmacy computer comprising:
  memory storing an encryption/decryption module and the public key;
  a processor in communication with memory;
  a near-field communications (NFC) transceiver in data communication with the processor and memory; and
  wherein the memory stores instructions which are executed by the processor to:
   establish an NFC communication link with the NFC tag via the NFC transceiver of the pharmacy computer,
   authenticate the medication package in accordance with the anti-counterfeiting data,
   encrypt, via the encryption/decryption module using the public key,
   the prescription data and the patient data,
   write the encrypted prescription data and the encrypted patient data to the NFC tag via the NFC transceiver;
   determine that the medication package is counterfeit in accordance with the anti-counterfeiting data via the public key; and
   generate an alert on a display of the pharmacy computer indicating a presence of the counterfeit medication package.

2. The system of claim 1, wherein the memory further stores instructions executed by the processor to:
 determine, in accordance with the medication data, that a medication alert exists;
 generate an alert notification in accordance with the determined medication alert; and
 communicate the generated alert notification to the user device via the secure communications link over the computer network.

3. The system of claim 2, wherein the memory further stores instructions executed by the processor to:
 analyze feedback data received from a plurality of disparate user devices via the computer network;
 determine at least one side effect identified from the analyzed feedback data;
 generate a notification inclusive of the determined at least one side effect; and
 communicate the generated side effect notification to at least one of the plurality of disparate user devices via the secure communications link over the computer network, wherein the at least one of the plurality of disparate user devices is selected in accordance with corresponding patient data and prescription data associated with the selected at least one of the plurality of user devices.

4. The system of claim 2, wherein the NFC tag comprises:
 a transceiver;
 memory storing medication data, encrypted prescription data, anti-counterfeit data, and encrypted patient data; and
 a processor in communication with the memory, wherein the memory stores instructions executed by the processor to:
  establish a near-field communication link (NFC) with a pharmacy computer,
  communicate the stored medication data and anti-counterfeiting data to the pharmacy computer,
  receive the encrypted prescription data and the encrypted patient data via the near-field communications link from the pharmacy computer into the memory,
  establish an NFC communication link, via the transceiver, with the user device, and
  communicate the stored medication data, prescription data, anti-counterfeit data, a secure URL, and patient data to the user device.

5. The system of claim 4, wherein the user device comprises:
 a processor;
 a display in communication with the processor;
 an NFC transceiver in communication with the processor; and memory in communication with the processor, wherein the memory stores instructions which are executed by the processor to:
  establish the NFC communication link with the NFC tag via the NFC transceiver of the user device,
  read, from the NFC tag via the NFC communication link, data from the tag, the data including the medication data, the secure URL, the encrypted patient data, and the encrypted prescription data,
  establish a secure communication link with the server in accordance with the secure URL,
  communicate the encrypted patient data and the encrypted prescription data to the server via the secure communication link,
  receive, from the server via the secure communication link, personalized guidance and engagement data corresponding to the patient data and the prescription data, and
  display the personalized guidance and engagement data via a graphical user interface of the display.

6. The system of claim 5, wherein the memory of the user device further stores instructions which are executed by the processor to receive, from the server, a medication alert; responsive to the medication alert, generate a notification via the display corresponding to the medication alert.

7. The system of claim 6, wherein the memory of the user device further stores instructions which are executed by the processor to receive, via a graphical user interface displayed on the display of the user device, user feedback; and communicate the received user feedback to the server via the secure communication link.

8. The system of claim 7, wherein the secure URL corresponds to a secure HTTPS website hosted by the server.

9. A near-field communication (NFC)-enabled medication packaging method, comprising:
  initializing, with a processor of a server associated with a pharmaceutical company, a tag of a medicine package with medication data corresponding to a medication contained therein, wherein initializing the tag further comprises writing each of a medication name, a medication packaging, a batch number, and an expiration date on the tag via an NFC communications link;
  signing the tag, by the server, using a private key to establish authentication of the medication contained in the medicine package;
  receiving data encrypted with a public key associated with the private key from a user device of an associated patient via a secure communications link over a computer network, the encrypted data including feedback data representative of a use of the medication by the patient and at least one of prescription data and patient data;
  decrypting the received encrypted data via the private key to retrieve the feedback data and the at least one of the prescription data and the patient data;
  analyzing the retrieved feedback data;
  generating personalized guidance specific to the patient in accordance with the analyzed feedback data and at least one of the prescription data and the patient data; and
  communicating, via the secure communications link over the computer network, the personalized guidance specific to the patient to the user device,
    wherein at least one of the initializing, signing, decrypting, generating, and communicating is performed by the processor of the server; and the method further comprises, with a pharmacy computer separate from the server:
      establishing an NFC communication link with the tag via an NFC transceiver of the pharmacy computer,
      authenticating the medication package in accordance with anti-counterfeiting data,
      encrypting, via an encryption/decryption module of the pharmacy computer using the public key, the prescription data and the patient data,
      writing the encrypted prescription data and the encrypted patient data to the tag via the NFC transceiver;
      determining that the medication package is counterfeit in accordance with the anti-counterfeiting data via the public key; and
      generating an alert on a display of the pharmacy computer indicating a presence of the counterfeit medication package.

10. The method of claim 9, further comprising:
  determining, in accordance with the medication data, that a medication alert exists;
  generating an alert notification in accordance with the determined medication alert; and
  communicating the generated alert notification to the user device via the secure communications link over the computer network.

11. The method of claim 10, further comprising:
  analyzing feedback data received from a plurality of disparate user devices via the computer network;
  determining at least one side effect identified from the analyzed feedback data;
  generating a notification inclusive of the determined at least one side effect; and
  communicating the generated side effect notification to at least one of the plurality of disparate user devices via the secure communications link over the computer network, wherein the at least one of the plurality of disparate user devices is selected in accordance with corresponding patient data and prescription data associated with the selected at least one of the plurality of user devices.

12. The method of claim 11, further comprising:
  communicating the stored medication data and anti-counterfeiting data from the tag to the pharmacy computer;
  receiving the encrypted prescription data and the encrypted patient data via the near-field communications link from the pharmacy computer into memory of the tag;
  establishing an NFC communication link between the tag and the user device via a transceiver of the NFC tag and a transceiver of the user device; and
  communicating the stored medication data, prescription data, anti-counterfeit data, a secure URL, and patient data to the user device.

13. The method of claim 12, wherein communicating the stored medication data, prescription data, anti-counterfeit data, secure URL, and patient data to the user device further comprises:
  reading, by the user device from the NFC tag via the NFC communication link, data from the tag, the data including the medication data, the secure URL, the encrypted patient data, and the encrypted prescription data;
  establishing a secure communication link between the user device and the server in accordance with the secure URL;
  communicating the encrypted patient data and the encrypted prescription data to the server from the user device via the secure communication link;

receiving, at the user device from the server via the secure communication link, personalized guidance and engagement data corresponding to the patient data and the prescription data; and displaying the personalized guidance and engagement data via a graphical user interface of a display of the user device.

14. The method of claim 13, further comprising:

receiving, from the server at the user device, a medication alert; and responsive to the medication alert, generating a notification via the display of the user device corresponding to the medication alert.

15. The method of claim 14, further comprising:

receiving, via a graphical user interface displayed on the display of the user device, user feedback; and communicating the received user feedback to the server via the secure communication link.

16. A computer-implemented method for near-field communication (NFC)-enabled medication packaging, comprising:

writing, via a server associated with a pharmaceutical company, each of a medication name, a medication packaging, a batch number, and an expiration date on an NFC tag of a medicine package with medication data corresponding to a medication contained therein;

signing the NFC tag using a private key to establish authentication of the medication contained in the medicine package;

receiving data encrypted with a public key associated with the private key from a user device of an associated patient via a secure communications link over a computer network, the encrypted data including at least one of prescription data and patient data;

decrypting the received data via the private key to retrieve the at least one of the prescription data and the patient data;

receiving, from the user device via the secure communications link over the computer network, user feedback data representative of a use of the medication by the patient;

analyzing the received feedback data;

generating personalized guidance specific to the patient in accordance with the analyzed user feedback data and at least one of the prescription data and the patient data;

communicating, via the secure communications link over the computer network, the personalized guidance specific to the patient to the user device;

establishing an NFC communication link with the NFC tag via an NFC transceiver of an associated pharmacy computer, authenticating the medication package in accordance with anti-counterfeiting data, encrypting, via an encryption/decryption module of the pharmacy computer using the public key, the prescription data and the patient data, writing the encrypted prescription data and the encrypted patient data to the NFC tag via the NFC transceiver;

determining that the medication package is counterfeit in accordance with the anti-counterfeiting data via the public key; and generating an alert on a display of the pharmacy computer indicating a presence of the counterfeit medication package.

17. The computer-implemented method of claim 16, further comprising:

determining, in accordance with the medication data, that a medication alert exists;

generating a notification in accordance with the determined medication alert; and communicating the generated alert notification to the user device via the secure communications link over the computer network.

18. The computer-implemented method of claim 17, further comprising:

analyzing feedback data received from a plurality of disparate user devices via the computer network;

determining at least one side effect identified from the analysis of feedback data;

generating a notification inclusive of the determined side effect; and communicating the generated side effect notification to at least one of the plurality of disparate user devices via the secure communications link over the computer network, wherein the at least one of the plurality of disparate user devices is selected in accordance with corresponding patient data and prescription data associated with the selected user device.

19. A near-field communication (NFC)-enabled medication packaging system, comprising:

a server associated with a pharmaceutical company, comprising:

a processor in communication with memory;

a near-field communications transceiver in data communication with the processor and memory; and a data storage in communication with the processor, the data storage storing a public key and a private key;

wherein the memory stores instructions which are executed by the processor to:

initialize a tag of a medicine package with medication data corresponding to a medication contained therein, wherein the tag of the medicine package is configured as an NFC-enabled, write-only tag affixed to the medicine package, the tag including a tag memory storing medicine data, the prescription data, and the patient data and wherein initializing the tag further comprises writing each of a medication name, a medication packaging, a batch number, and an expiration date on the tag via an NFC communications link, sign the tag using the private key to establish authentication of the medication contained in the medicine package, receive encrypted data from a user device of a patient via a secure communications link over a computer network, the encrypted data including feedback data representative of a use of the medication by the patient and at least one of prescription data and patient data, decrypt the received encrypted data to retrieve the feedback data and the at least one of the prescription data and the patient data, analyze the retrieved feedback data, generate personalized guidance specific to the patient in accordance with the analyzed feedback data and at least one of the prescription data and the patient data, and communicate, via the secure communications link over the computer network, the personalized guidance specific to the patient to the user device;

wherein at least one of the server or the tag are in communication with an associated pharmacy computer, the associated pharmacy computer configured to:
establish an NFC communication link with the NFC tag,
authenticate the medication package in accordance with the anti-counterfeiting data,
encrypt the prescription data and the patient data using the public key,
write the encrypted prescription data and the encrypted patient data to the NFC tag;
determine that the medication package is counterfeit in accordance with the anti-counterfeiting data via the public key; and
generate an alert indicating a presence of the counterfeit medication package.

20. A near-field communication (NFC)-enabled medication packaging system, comprising:
a server associated with a pharmaceutical company, comprising:
a processor in communication with memory;
a near-field communications transceiver in data communication with the processor and memory; and
a data storage in communication with the processor, the data storage storing a public key and a private key;
wherein the memory stores instructions which are executed by the processor to:
initialize a tag of a medicine package with medication data corresponding to a medication contained therein, wherein the tag of the medicine package is configured as an NFC-enabled, write-only tag affixed to the medicine package, the tag including a tag memory storing medicine data, the prescription data, and the patient data and wherein initializing the tag further comprises writing each of a medication name, a medication packaging, a batch number, and an expiration date on the tag via an NFC communications link,
sign the tag using the private key to establish authentication of the medication contained in the medicine package,
receive encrypted data from a user device of a patient via a secure communications link over a computer network, the encrypted data including feedback data representative of a use of the medication by the patient and at least one of prescription data and patient data,
decrypt the received encrypted data to retrieve the feedback data and the at least one of the prescription data and the patient data,
analyze the retrieved feedback data,
generate personalized guidance specific to the patient in accordance with the analyzed feedback data and at least one of the prescription data and the patient data, and
communicate, via the secure communications link over the computer network, the personalized guidance specific to the patient to the user device;
wherein the tag is configured to:
communicate the stored medication data and anti-counterfeiting data to an associated pharmacy computer for authentication thereof, via an NFC communication link;
receive prescription data and patient data encrypted using the public key from the associated pharmacy computer, and
store the encrypted prescription data and the encrypted patient data.

* * * * *